United States Patent
Bootwala et al.

(10) Patent No.: US 9,101,412 B2
(45) Date of Patent: Aug. 11, 2015

(54) VERTEBRAL ADJUSTMENT SYSTEMS FOR SPINE ALIGNMENT

(75) Inventors: Zoher Bootwala, West Chester, PA (US); Jason Banowetz, West Chester, PA (US); Darrell S. Hanson, Houston, TX (US)

(73) Assignee: DePuy Synthes Products, Inc., Raynham, MA (US)

( * ) Notice: Subject to any disclaimer, the term of this patent is extended or adjusted under 35 U.S.C. 154(b) by 207 days.

(21) Appl. No.: 13/228,871

(22) Filed: Sep. 9, 2011

(65) Prior Publication Data

US 2012/0197297 A1 Aug. 2, 2012

Related U.S. Application Data

(60) Provisional application No. 61/381,234, filed on Sep. 9, 2010.

(51) Int. Cl.
*A61B 17/58* (2006.01)
*A61B 17/70* (2006.01)

(52) U.S. Cl.
CPC ........... *A61B 17/7077* (2013.01); *A61B 17/708* (2013.01)

(58) Field of Classification Search
USPC ................................ 606/105, 86 A, 914, 916
See application file for complete search history.

(56) References Cited

U.S. PATENT DOCUMENTS

| | | | |
|---|---|---|---|
| 5,219,349 A * | 6/1993 | Krag et al. ....................... 606/53 |
| 5,478,340 A | 12/1995 | Kluger | |
| 6,090,113 A | 7/2000 | Le Couedic et al. | |
| 7,655,008 B2 | 2/2010 | Lenke et al. | |
| 7,758,584 B2 | 7/2010 | Bankoski et al. | |
| 8,475,467 B2 * | 7/2013 | Manninen ..................... 606/105 |
| 2004/0138661 A1 * | 7/2004 | Bailey .............................. 606/61 |
| 2004/0230191 A1 | 11/2004 | Frey et al. | |
| 2005/0192572 A1 * | 9/2005 | Abdelgany et al. ............. 606/61 |
| 2006/0195092 A1 | 8/2006 | Barry | |
| 2006/0271050 A1 | 11/2006 | Piza Vallespir | |
| 2007/0112351 A1 * | 5/2007 | Assell et al. ..................... 606/61 |
| 2007/0213715 A1 | 9/2007 | Bridwell et al. | |
| 2007/0213716 A1 | 9/2007 | Lenke et al. | |
| 2008/0294206 A1 | 11/2008 | Choi et al. | |
| 2009/0204159 A1 | 8/2009 | Justis et al. | |
| 2009/0216237 A1 | 8/2009 | Frezal et al. | |
| 2009/0228053 A1 | 9/2009 | Kolb et al. | |
| 2010/0298885 A1 | 11/2010 | Tribus | |
| 2010/0331849 A1 | 12/2010 | Riesinger et al. | |
| 2011/0172714 A1 * | 7/2011 | Boachie-Adjei et al. ...... 606/264 |
| 2012/0071885 A1 * | 3/2012 | Forton et al. ................... 606/104 |
| 2013/0096624 A1 * | 4/2013 | Di Lauro et al. ............... 606/279 |

FOREIGN PATENT DOCUMENTS

WO WO 2009/158707 12/2009
WO WO 2012/034005 3/2012

OTHER PUBLICATIONS

International Patent Application No. PCT/US2011/050977: International Search Report and Written Opinion dated Mar. 5, 2012, 20 pages.

* cited by examiner

*Primary Examiner* — Jan Christopher Merene
(74) *Attorney, Agent, or Firm* — Baker & Hostetler LLP

(57) ABSTRACT

A vertebral adjustment system configured to move individual vertebral bodies relative to the other vertebral bodies to thereby realign the spine. The system may include a frame, and a plurality of alignment devices coupled to the frame and to the individual vertebral bodies. By manipulated the alignment devices the vertebral bodies to which they are attached may be moved.

23 Claims, 28 Drawing Sheets

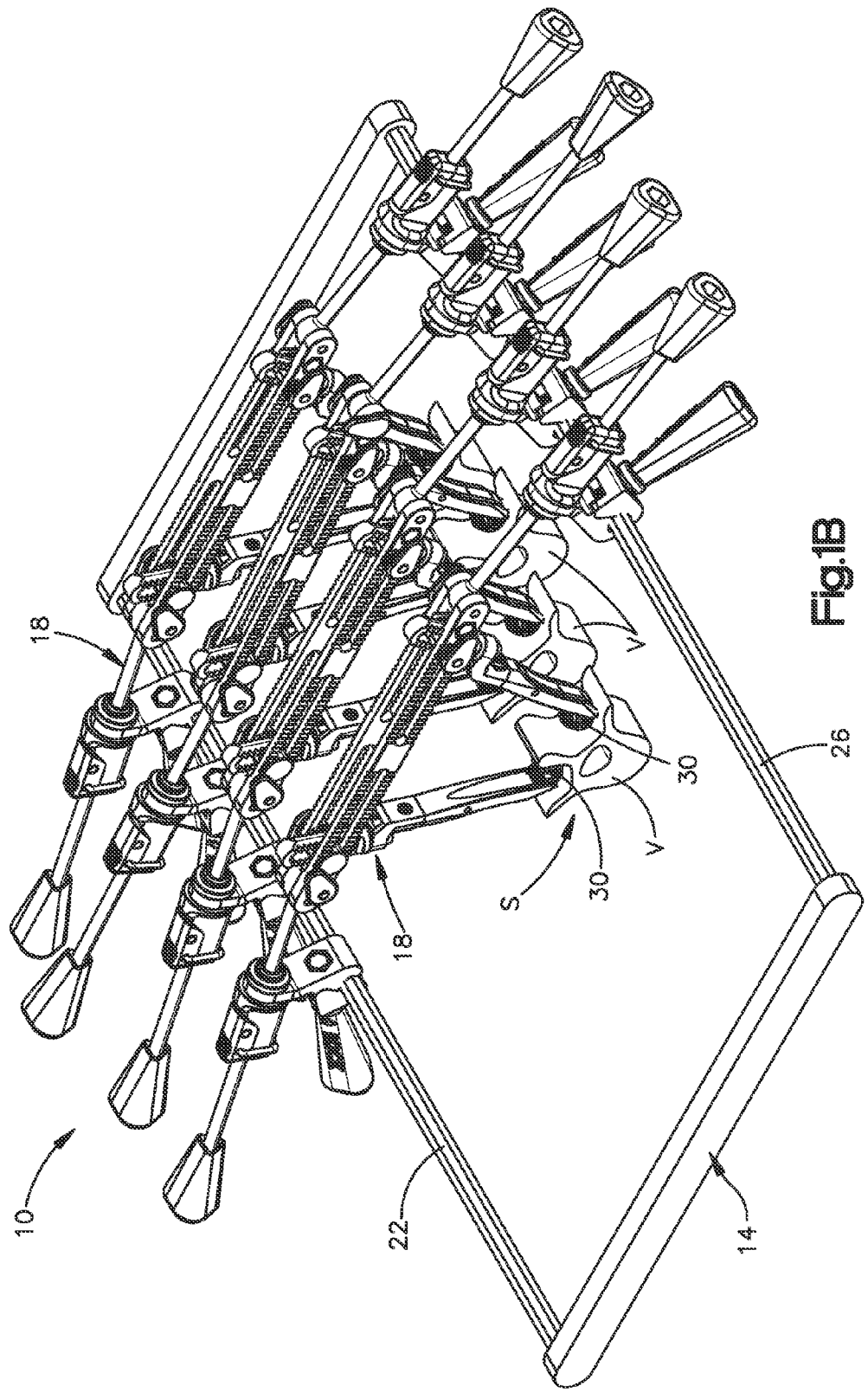

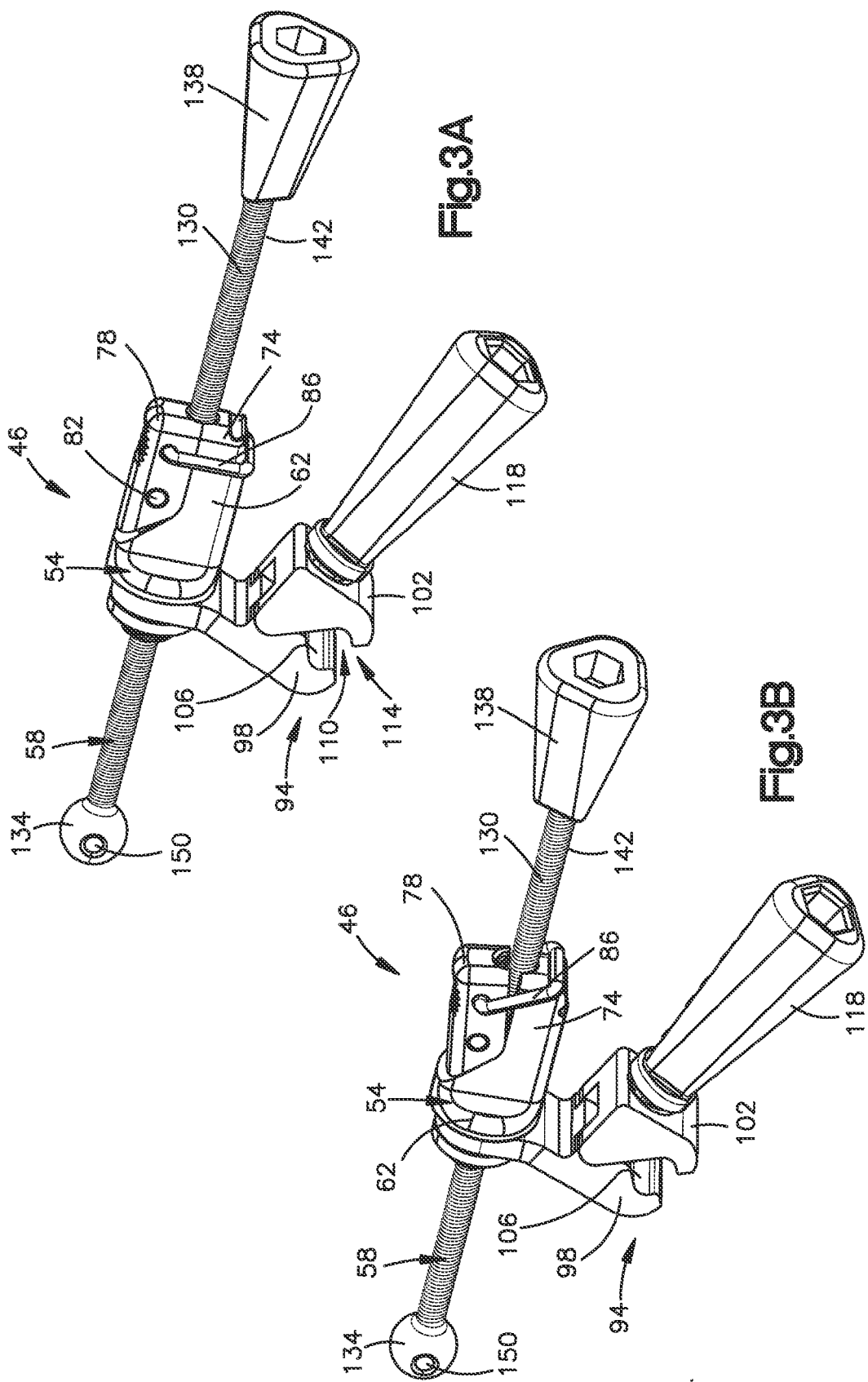

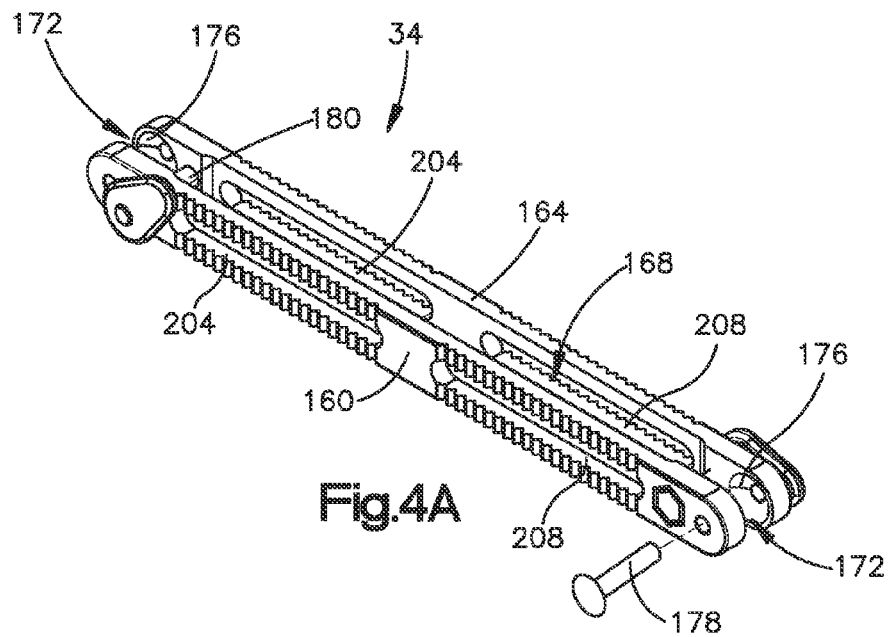
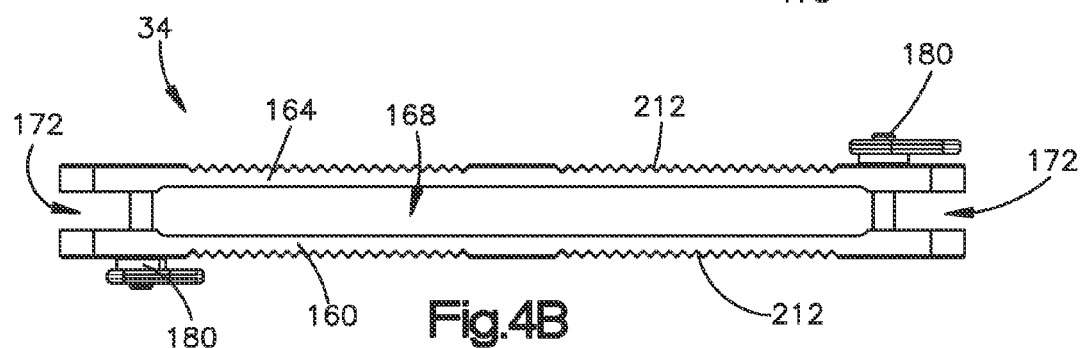
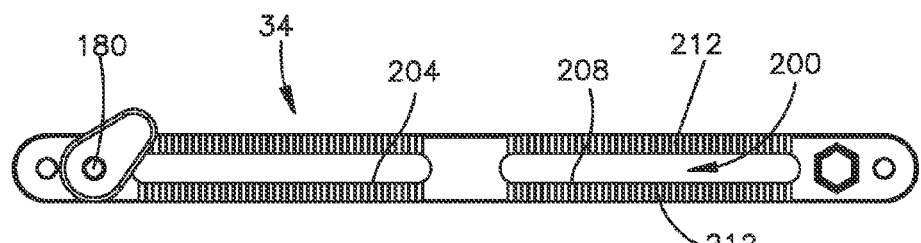

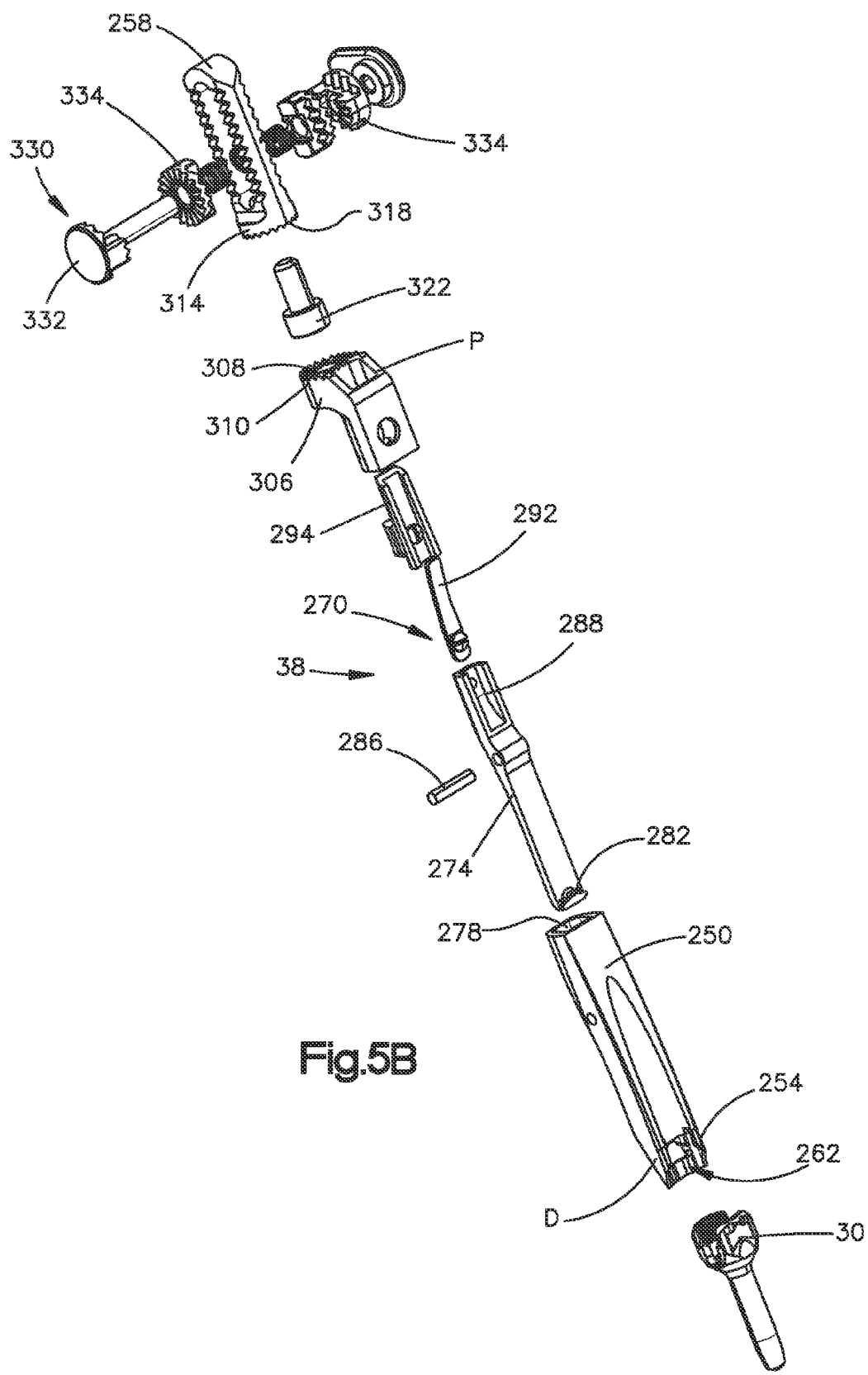

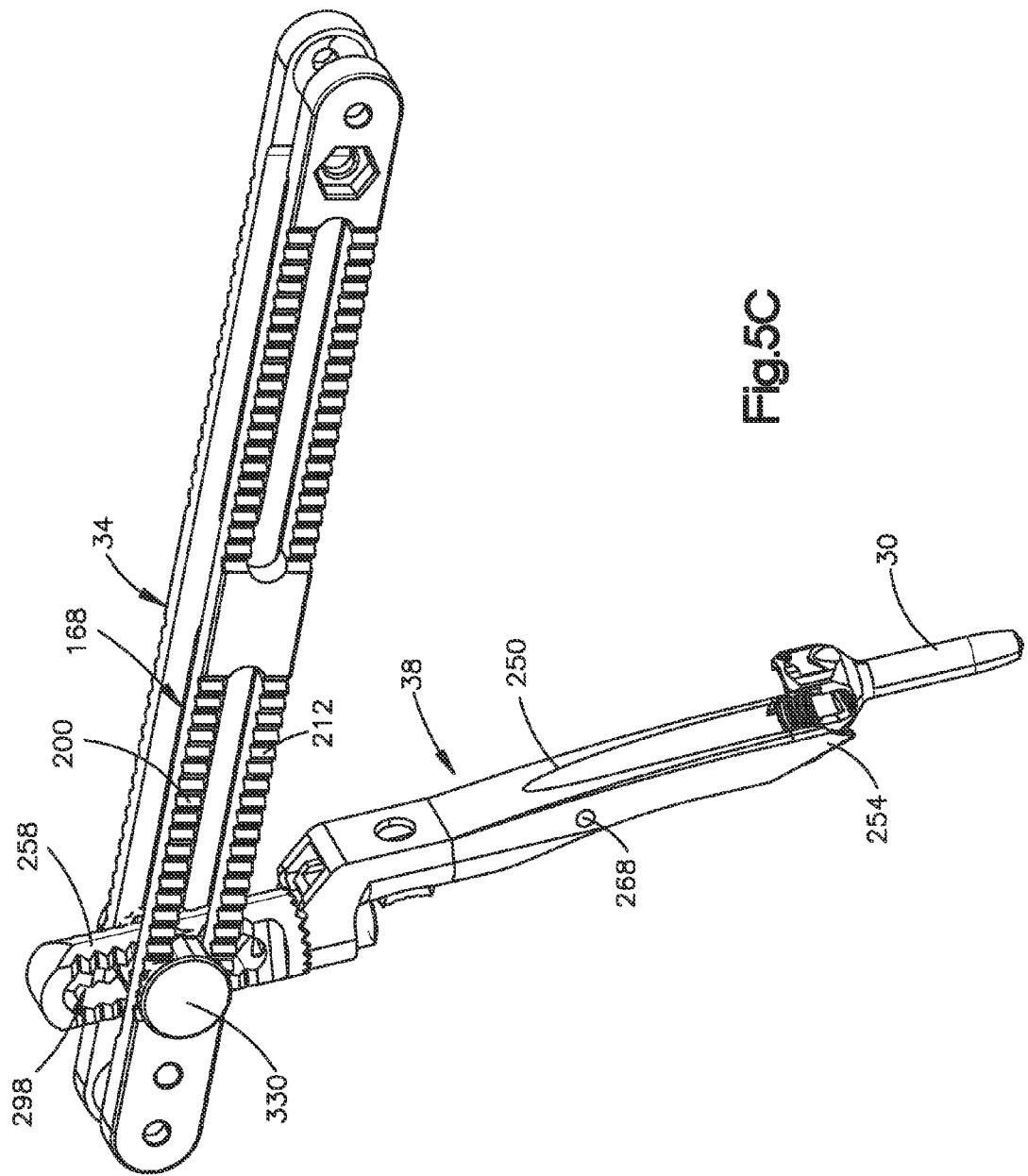

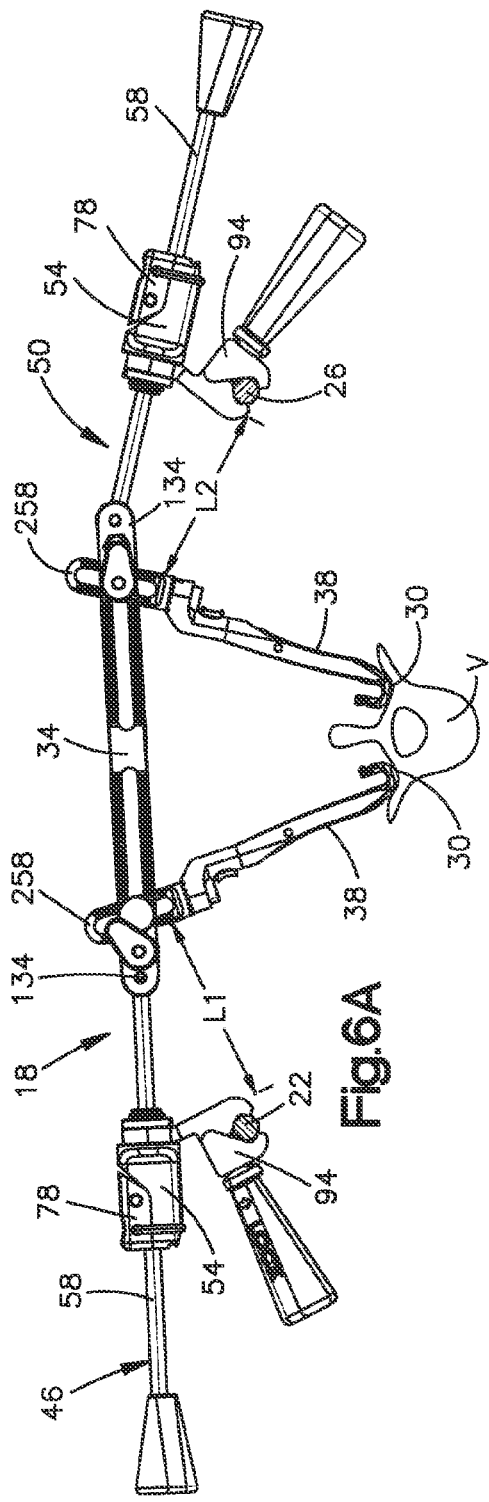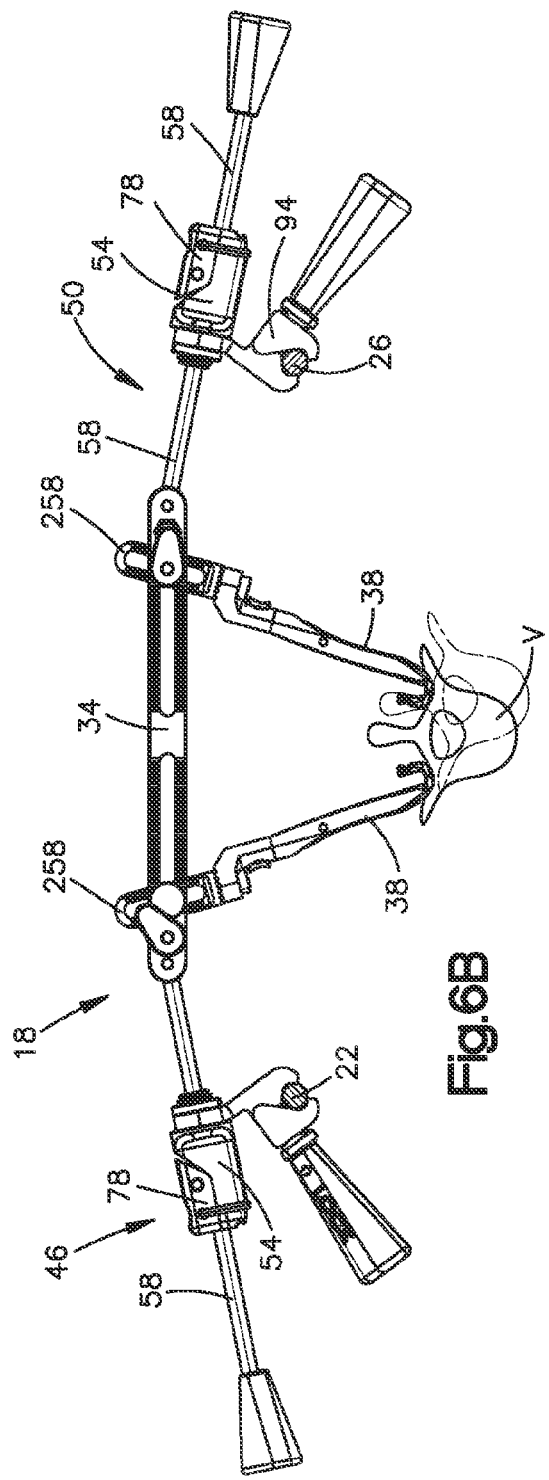

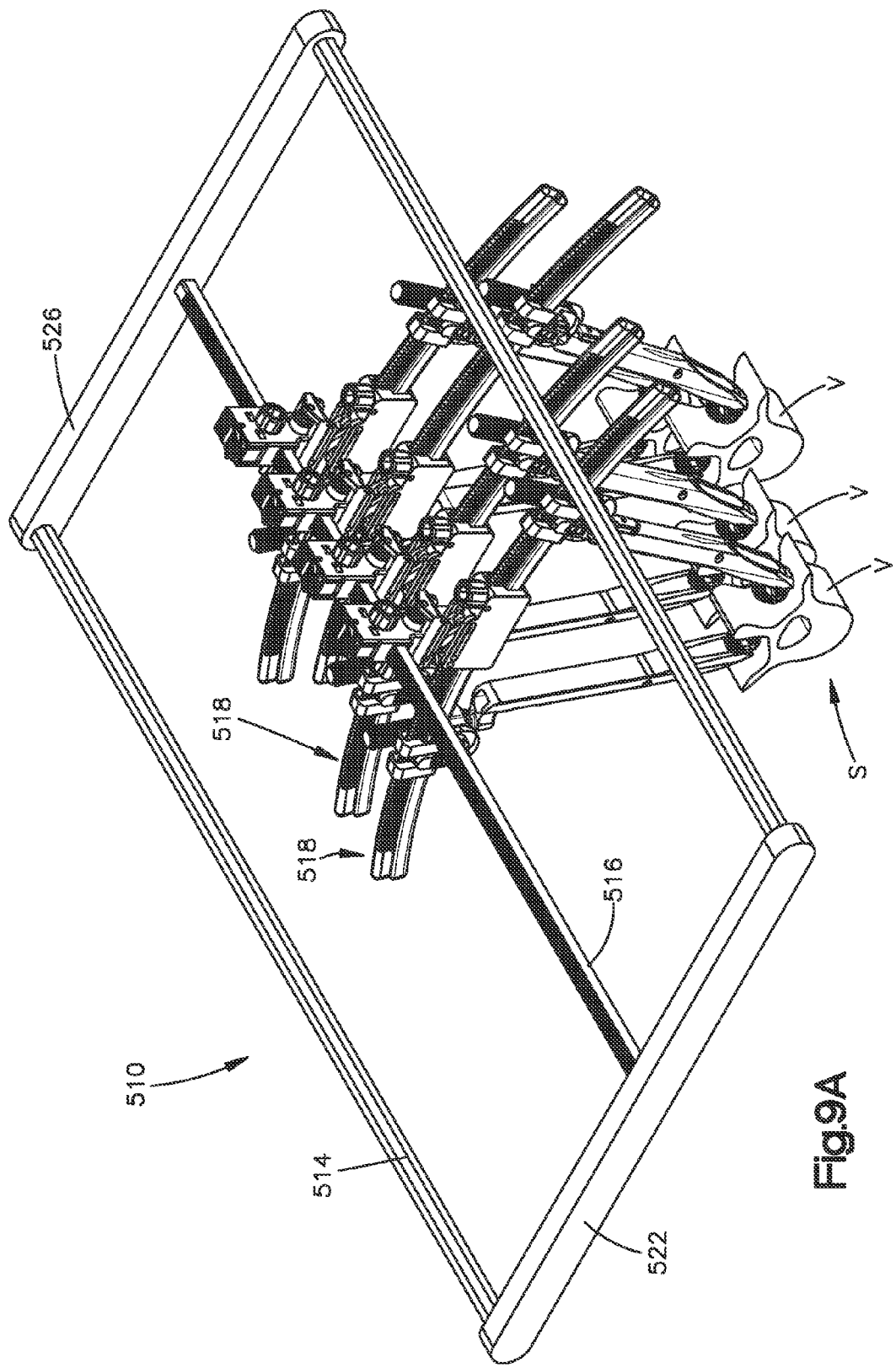

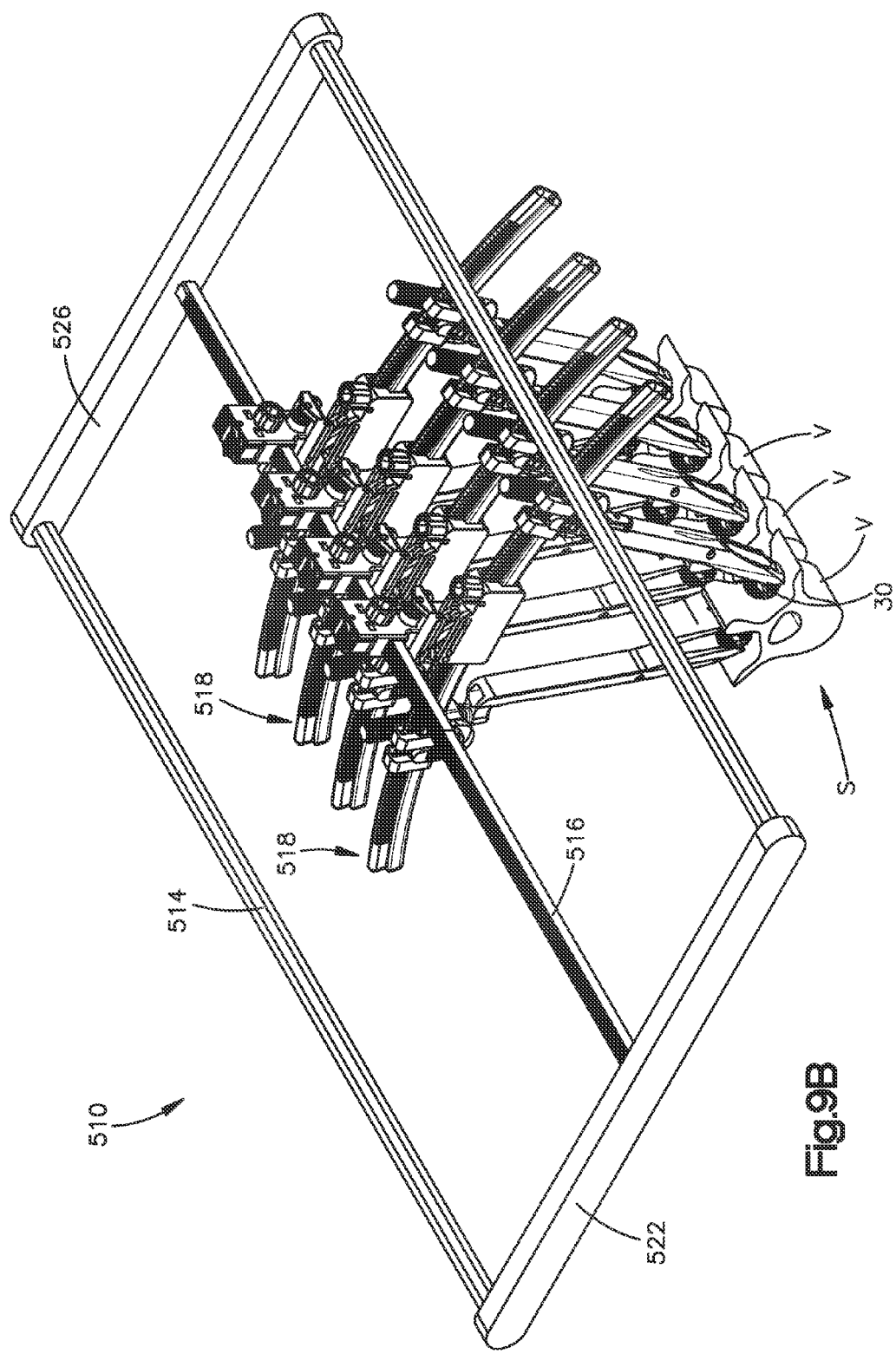

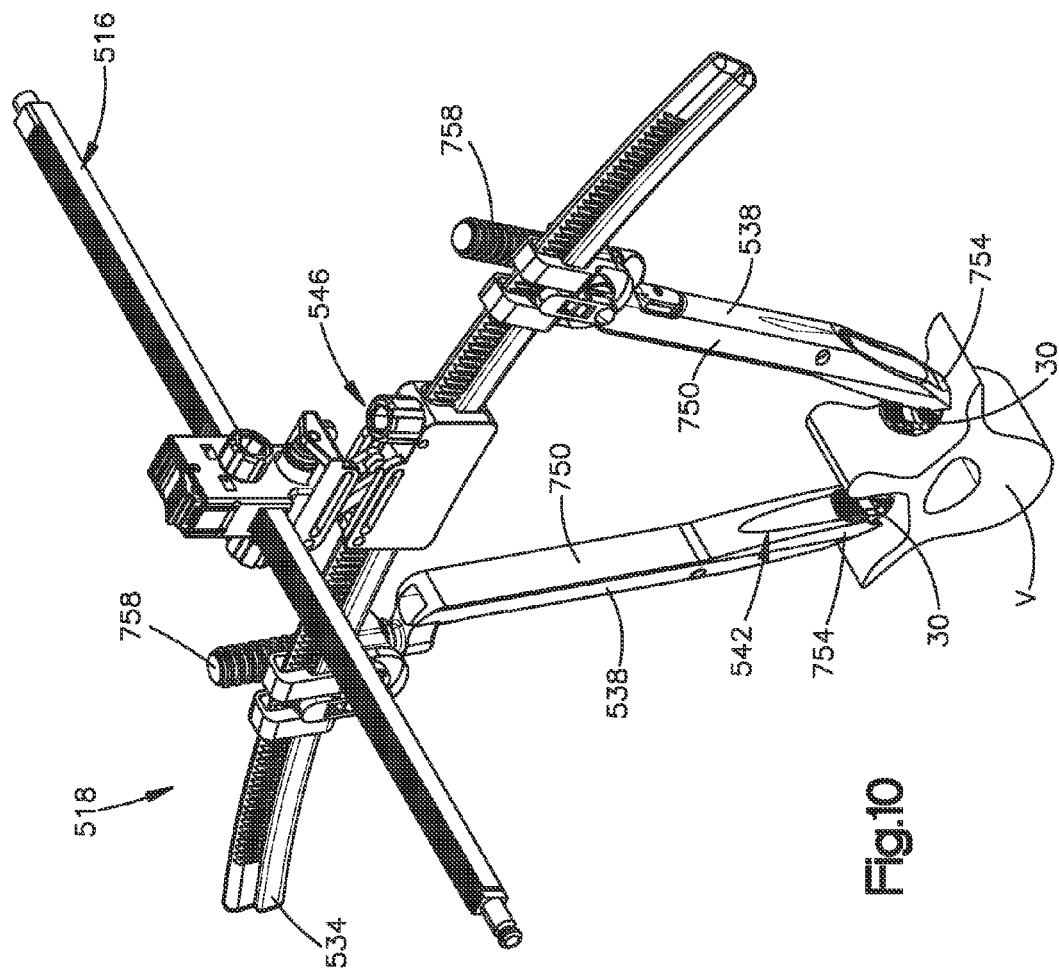

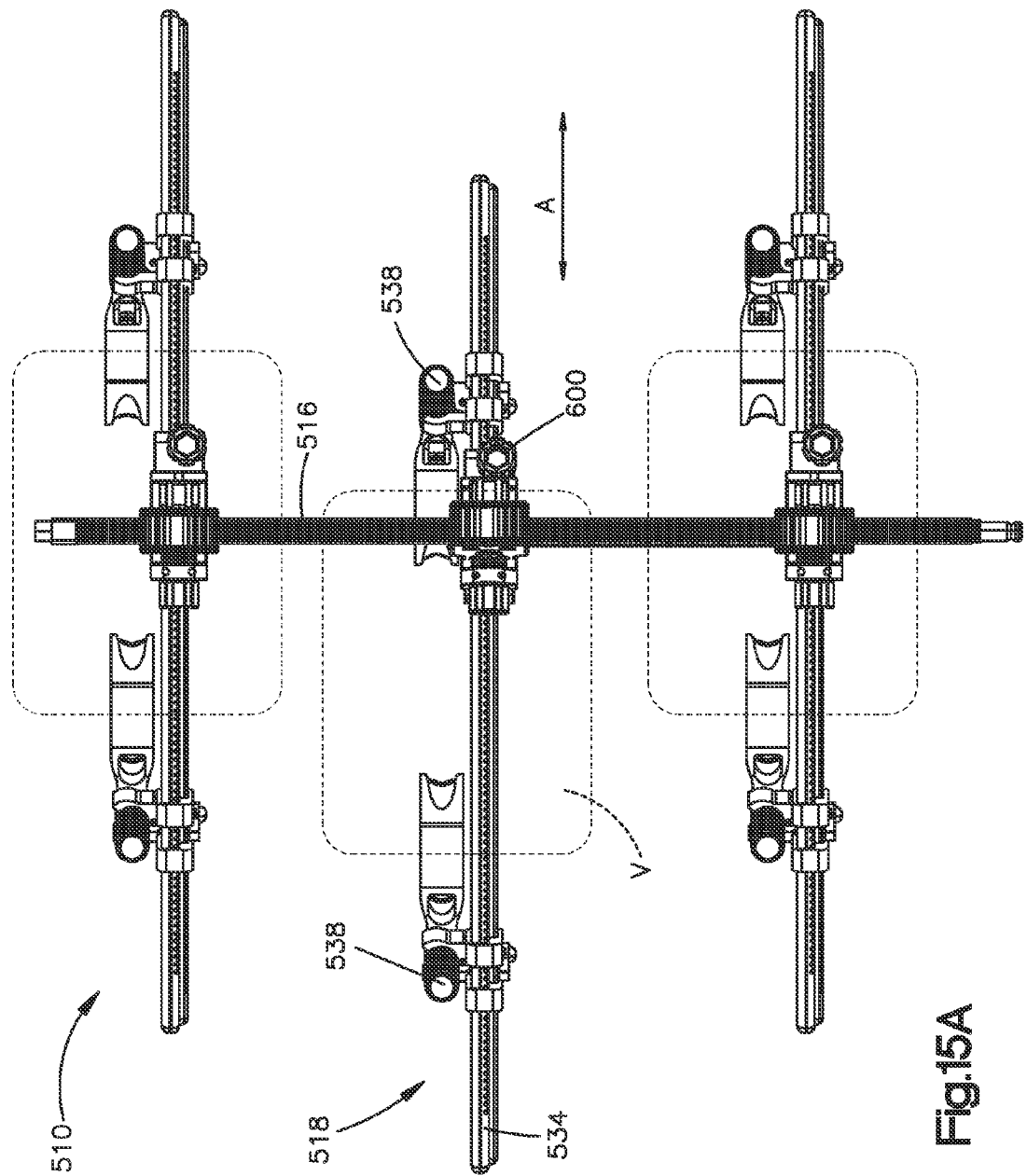

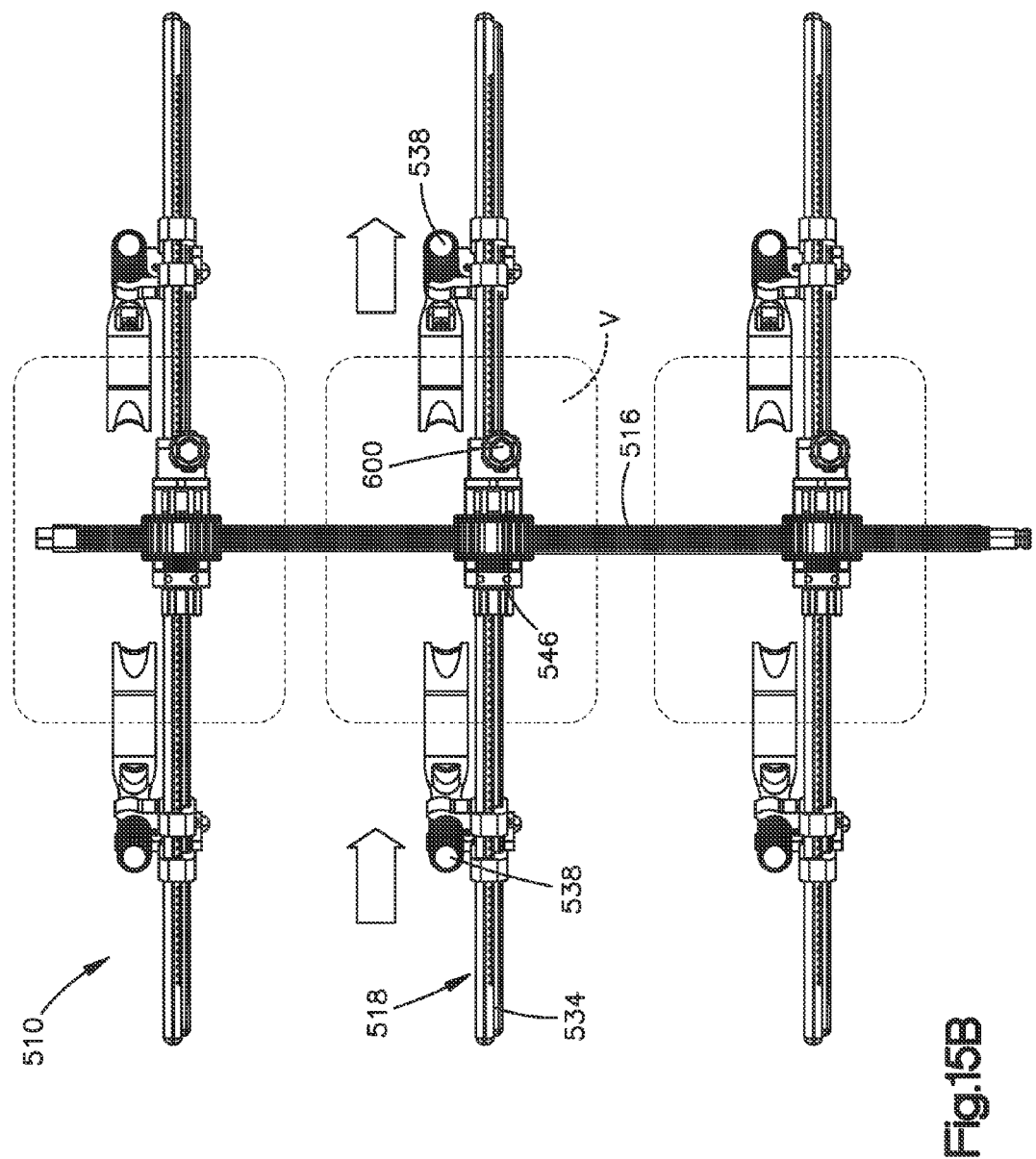

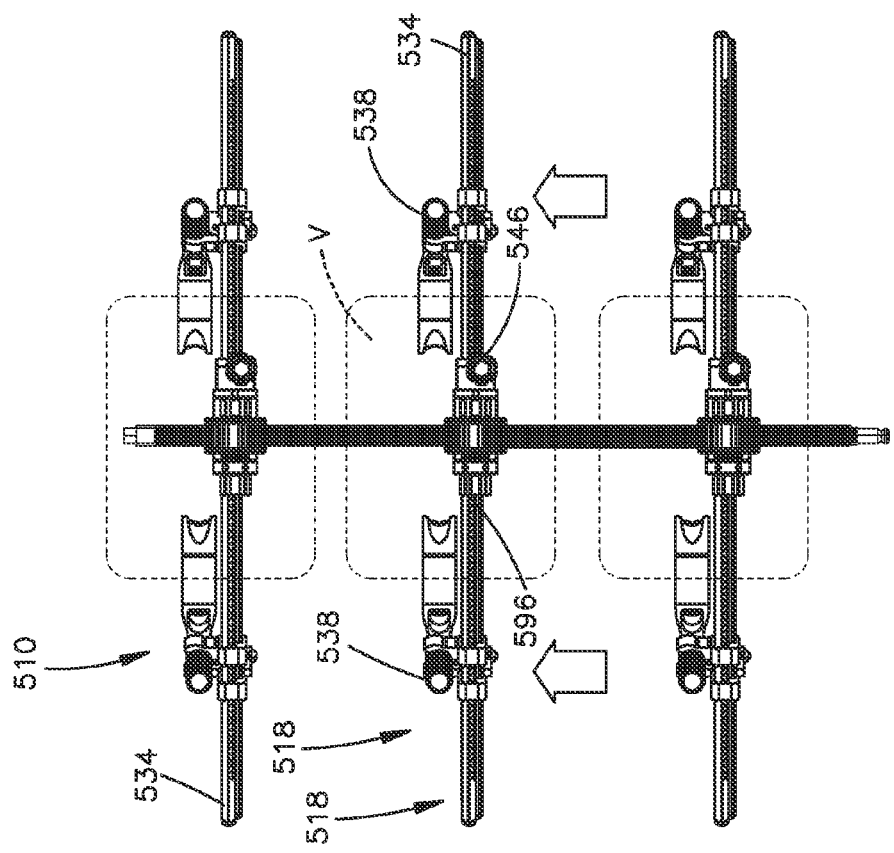
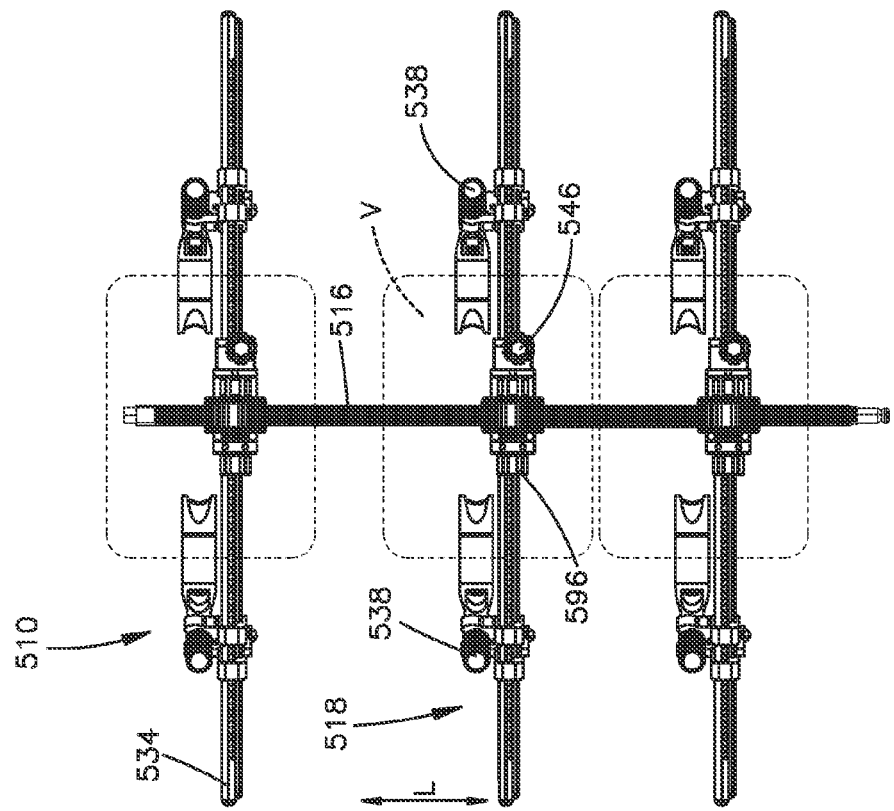

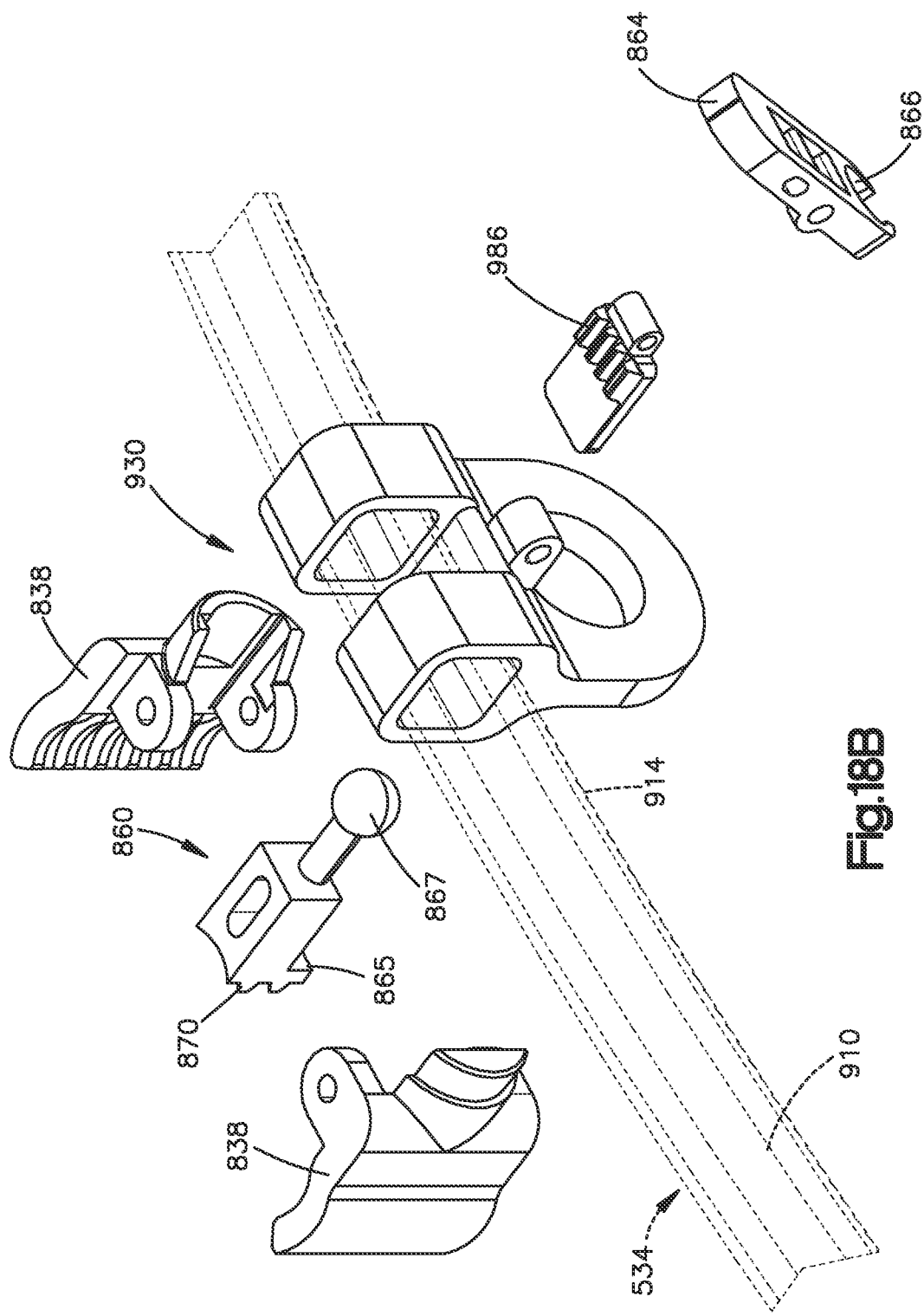

VERTEBRAL ADJUSTMENT SYSTEMS FOR SPINE ALIGNMENT

CROSS-REFERENCE TO RELATED APPLICATIONS

This application claims the benefit of U.S. patent application Ser. No. 61/381,234, filed Sep. 9, 2010, the disclosure of which is hereby incorporated by reference as if set forth in its entirety herein.

BACKGROUND

Spinal deformities of varying etiologies are well known. Such deformities include abnormal spinal curvatures, such as, for example, scoliosis, kyphosis, or other abnormal curvatures wherein natural alignment of the spine is altered. Specifically, scoliotic deformities can be separated into abnormal translation and/or rotation of the vertebrae in each of the coronal, transverse, and sagittal planes. Therefore, treatment of certain spinal deformities such as scoliosis may require addressing reduction of the abnormal curvature in each of the three spatial planes.

A number of methods and techniques have been used to reduce abnormal spinal curvatures. Several of these techniques have been based on anchoring a devise onto posterior elements of the spine. Such techniques may reduce the certain translational aspects of the deformity, but have little or no effect on the rotational aspects.

Additionally, pedicle screws have been used in the treatment of abnormal spinal curvatures. Such techniques are based on translation to align the spinal column, either by bending or rotating a fixation rod after the rod is engaged to the pedicle screws, or by forcing the pedicle screws into engagement with the rod. Other reduction techniques provide for derotation via the use of pedicle screws, but such derotation is usually implemented following placement of the fixation rod.

SUMMARY

In one embodiment, a vertebral adjustment system includes a frame, and an alignment device configured to be coupled to the frame. The frame includes opposed first and second sides. The alignment device includes a first leg, a second leg, a first adjustment arm, and a second adjustment arm. The first leg includes a first end that is configured to be coupled to a respective bone anchor, and a second end spaced from the first end. The second leg includes a first end that is configured to be coupled to a respective bone anchor, and a second end spaced from the first end. The first adjustment arm includes a first elongate member that couples to the first side of the frame and is pivotal relative to the second end of the first leg. A first length is defined between the second end of the first leg and the first side of the frame, and the first length is adjustable. The second adjustment arm includes a second elongate member that couples to the second side of the frame and is pivotal relative to the second end of the second leg. A second length is defined between the second end of the second leg and the second side of the frame, and the second length is adjustable.

In another embodiment, a vertebral adjustment system includes an axial member, and alignment device configured to be coupled to the axial member. The axial member is positionable at a location adjacent to a spine so as to extend along a first direction. The alignment device includes a cross-bar, and an adjustment mechanism. The cross-bar is configured to be coupled to a vertebral body, and extends along a second direction substantially transverse to the first direction. The adjustment mechanism defines a first channel that receives the axial member to thereby couple the adjustment mechanism to the axial member, and a second channel that is substantially transverse to the first channel and receives the cross-bar such that the cross-bar can be selectively translated through the second channel along a second direction that is substantially transverse to the first direction, thereby moving the vertebral body along the second direction when the cross-bar is coupled to the vertebral body.

In another embodiment, a method of adjusting the position of a vertebral body of a spine includes attaching first and second bone anchors to the vertebral body, coupling a first leg to the first bone anchor and a second leg to the second bone anchor, such that the first and second legs extend posteriorly from the vertebral body, coupling a cross-bar to the first and second legs, and activating an adjustment mechanism to translate the cross-bar relative to the adjustment mechanism so as to move the vertebral body in the medial-lateral direction.

BRIEF DESCRIPTION OF THE DRAWINGS

The foregoing summary, as well as the following detailed description of exemplary embodiments, will be better understood when read in conjunction with the appended drawings, in which there is shown in the drawings example embodiments for the purposes of illustration. It should be understood, however, that the application is not limited to the precise arrangements and systems shown. In the drawings:

FIG. 1B is a perspective view of an alignment system constructed in accordance with an embodiment, the alignment system includes a frame and a plurality alignment devices attached to the frame and to respective vertebral bodies so as to be capable of adjusting each vertebral body to thereby realign the spine;

FIG. 3A is a perspective view of one of the adjustment arms shown in FIG. 2, the adjustment arm including a medial housing and an elongate member that is translatable through the medial housing;

FIG. 3B is a perspective view of the adjustment arm shown in FIG. 3A with the medial housing in an open position so as to allow the elongate member to freely translate through the medial housing;

FIG. 4A is a perspective view of the cross-bar shown in FIG. 2;

FIG. 4B is a top plan view of the cross-bar shown in FIG. 4A;

FIG. 4C is a side elevation view of the cross-bar shown in FIG. 4A;

FIG. 5B is an exploded view of the leg shown in FIG. 5A;

FIG. 5C is a perspective view of the leg shown in FIG. 5A attached to the cross-bar shown in FIG. 4A;

FIG. 6A is a side elevation view of the alignment device shown in FIG. 2 attached to a misaligned vertebral body;

FIG. 6B is a side elevation view of the alignment device shown in FIG. 6A after the vertebral body has been moved;

FIG. 9A is a perspective view of an alignment system constructed in accordance with another embodiment, the alignment system includes a main axial member and a plurality of alignment devices attached to the main axial member and to respective vertebral bodies so as to be capable of adjusting each vertebral body to thereby realign the spine;

FIG. 9B is a perspective view of the alignment system shown in FIG. 9A after the vertebral bodies have been adjusted and the spine realigned;

FIG. 10 is a perspective view of one of the alignment devices shown in FIG. 9A, the alignment device including a pair of legs that extend from the vertebral body, a cross-bar coupled to the legs, and an adjustment mechanism coupled to the main axial member and to the cross-bar such that the cross-bar can translate through the adjustment mechanism;

FIG. 15A is a top plan view of the adjustment system shown in FIG. 9A coupled to three vertebral bodies, one of the vertebral bodies being laterally misaligned with respect to the other two vertebral bodies;

FIG. 15B is a top plan view of the adjustment system shown in FIG. 15A after the laterally misaligned vertebral body has been moved along a lateral direction to thereby realign the vertebral bodies;

FIG. 16A is a top plan view of the adjustment system shown in FIG. 9A coupled to three vertebral bodies, one of the vertebral bodies being longitudinally misaligned with respect to the other two vertebral bodies;

FIG. 16B is a top plan view of the adjustment system shown in FIG. 16A after the longitudinally misaligned vertebral body has been moved along the longitudinal direction;

FIG. 18B is a partial exploded view of one of the legs of the adjustment system shown in FIG. 18A being coupled to the cross-bar.

DETAILED DESCRIPTION OF ILLUSTRATIVE EMBODIMENTS

Figure 1A:
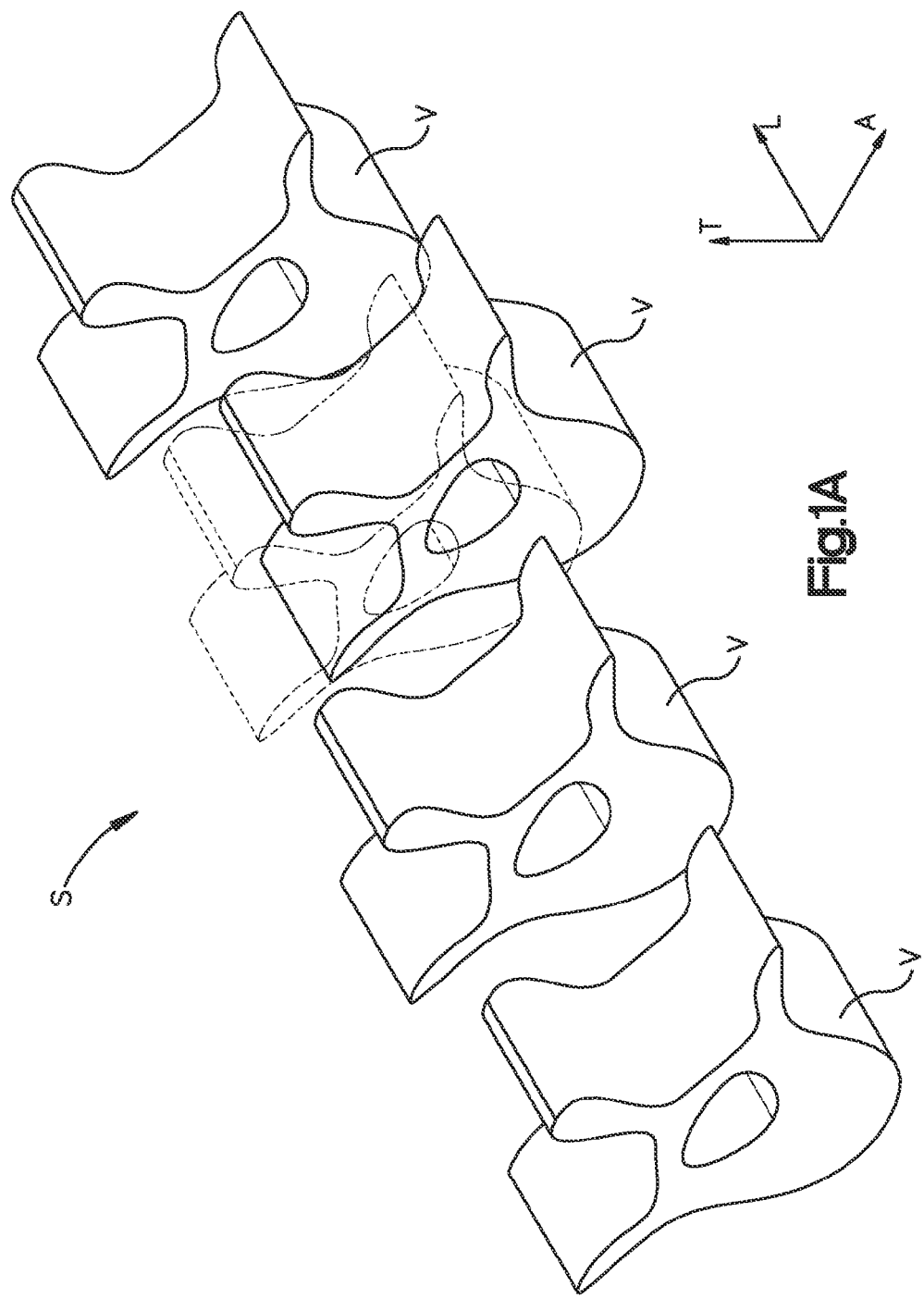
FIG. 1A is a partial perspective view of a plurality of schematic vertebral bodies of a spine, one of the vertebral bodies being misaligned relative to the others.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the system and related parts thereof. The words, "anterior", "posterior", "superior," "inferior," "medial," "lateral," and related words and/or phrases are used to designate various positions and orientations in the human body to which reference is made and are not meant to be limiting. The terminology includes the above-listed words, derivatives thereof and words of similar import.

Referring to FIG. 1A, a spine "S" includes a number of vertebral bodies "V" that have a height that generally extends in a first or longitudinal or caudal-cranial direction "L" a length that generally extends in a second or lateral or medial-lateral direction "A" and a width that generally extends in a third or transverse or anterior-posterior direction "T." It should be appreciated therefore, that the longitudinal "L" and transverse "T" directions extend along a vertical plane, the longitudinal "L" and lateral "A" directions extend along a lateral plane, and the lateral "A" and transverse "T" directions extend along a transverse plane. In a misaligned spine such as scoliotic spine "S" shown in FIG. 1A, the natural position and alignment of the vertebral bodies "V" are altered due to abnormal vertebral rotation and translation. As a result, an anterior-posterior axes of the vertebral bodies "V", which are normally positioned within a common vertical plane (i.e. the midline sagittal plane), may be non-coplanar (i.e. extend along multiple planes). Additionally, there may be an abnormal divergence (or convergence) of the anterior-posterior axes of the vertebral bodies "V".

Figure 1C:
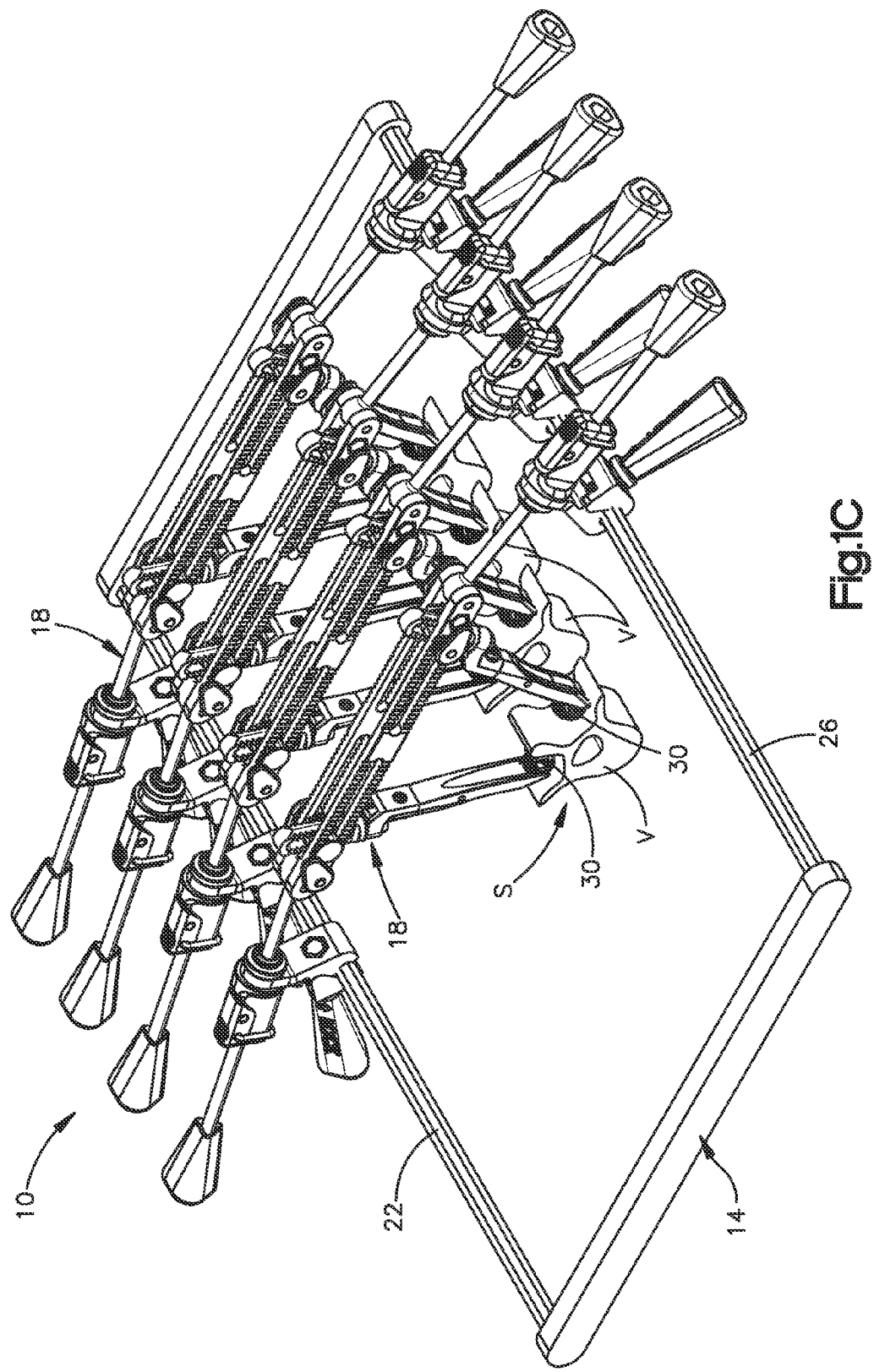
FIG. 1C is a perspective view of the alignment system shown in FIG. 1B after the vertebral bodies have been adjusted and the spine realigned.

Referring also to FIGS. 1B and 1C, a vertebral adjustment system 10 is configured to manipulate the alignment of the vertebral bodies "V" of the spine "S" to realign them into a desired orientation. As shown, the adjustment system 10 includes a frame 14, at least one pair, such as a plurality of pairs of bone anchors 30, and at least one, such as a plurality of alignment devices 18 that are coupled to the frame 14 and to the bone anchors. Each alignment device 18 is configured to be affixed to a respective vertebral body "V" so as to allow alignment of individual vertebral bodies "V" relative to the other vertebral bodies "V". The frame 14 may be constructed in the shape of a rectangle or any suitable alternative shape, and can include a first side 22 and an opposed second side 26 that can extend substantially parallel to the first side 22 that are configured to provide substantially parallel support members or rods for connection of the alignment devices 18. Each alignment device 18 can be configured to be coupled to a respective pair of bone anchors 30, which are illustrated as pedicle screws that have been implanted into the vertebral bodies "V". The frame 14 is typically not connected to an external frame such as a bed frame, but in some circumstances, may be. The frame 14 is placed over the spine such that the first and second sides 22 and 26 are on opposed sides of the spine and extend along the spine in the longitudinal direction. With proper positioning, several vertebral bodies may have a respective alignment device 18 attached to it and the first and second sides 22 and 26 of the frame 14. The frame 14 and the alignment devices 18 may be constructed of stainless steel, titanium, CoCrM, carbon fiber, or other appropriate materials. As shown in FIG. 1C, and will be described in more detail below, the vertebral bodies "V" may be aligned (e.g. rotated, moved laterally or medially, anteriorly or posteriorly) via various pivotal connections of the alignment devices 18.

Figure 2:
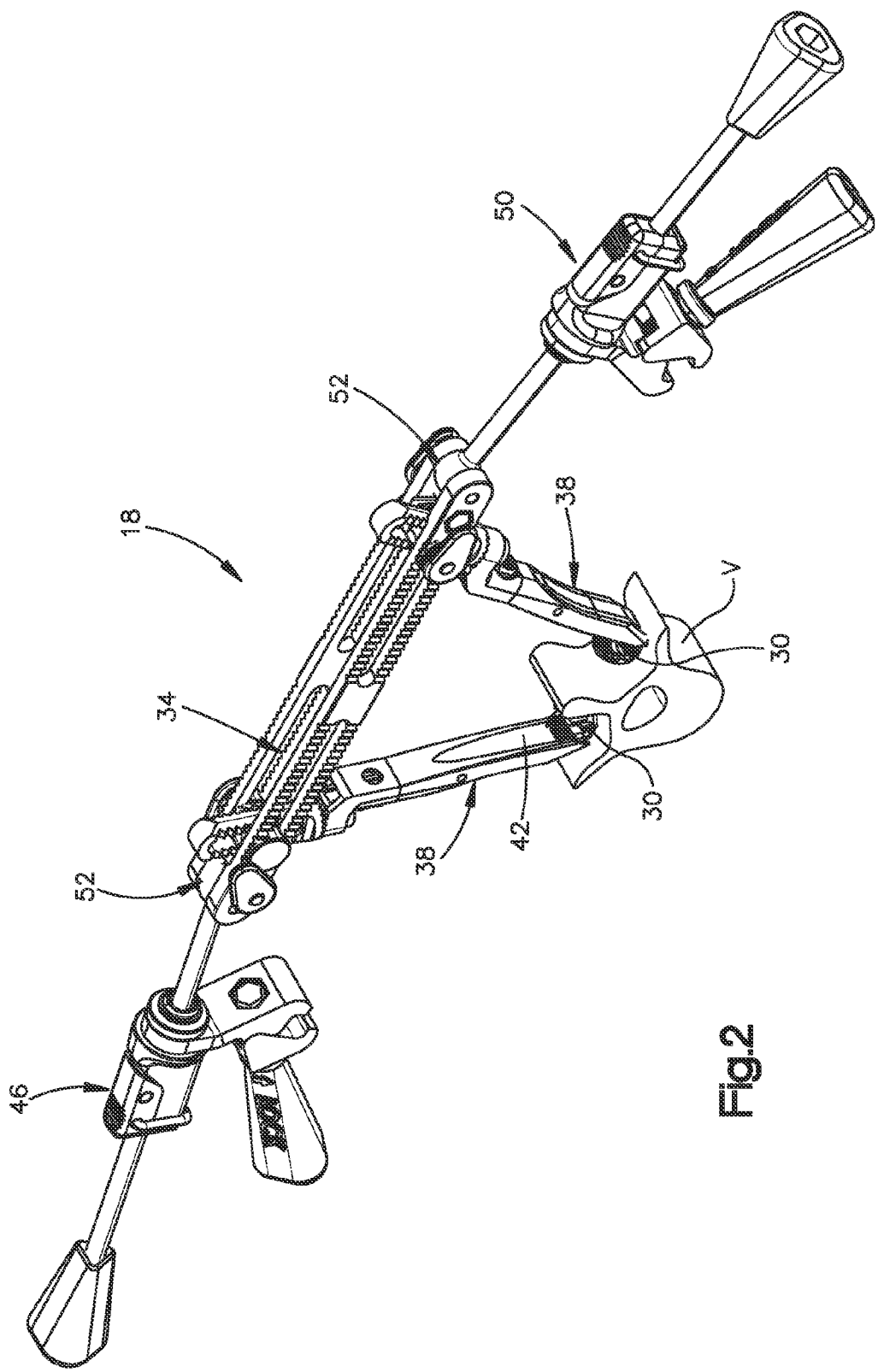
FIG. 2 is a perspective view of one of the alignment devices shown in FIG. 1B, the alignment device including a pair of legs that extend from the vertebral body, a cross-bar coupled to the legs, and a pair adjustment arms pivotally coupled to the cross-bar.

As shown in FIG. 2, each alignment device 18 can include a cross-bar 34, and a pair of legs 38 that are coupled to the cross-bar 34 and to respective bone anchors 30 that are implanted into the vertebral body "V". As shown in FIG. 2, the bone anchors 30 are implanted into the vertebral body "V" proximate to the pedicles on either side of the spinous process. A shown, each bone anchor 30 includes a head portion that defines a channel. The legs 38 each have a first or distal end that attaches to the head portions of the bone anchors 30 and a second end that is spaced apart from the first ends. The legs 38 extend from the bone anchors 30 such that each leg 38 is substantially parallel to the bone anchor 30 that it is attached. Generally, the legs 38 extend from the bone anchors 30 in substantially the transverse direction. That is, the legs 38 extend from the bone anchors 30 such that at least some component of the direction that the legs 38 extend is in the transverse direction. Therefore, the legs 38 may be parallel to each other or they may diverge from each other as they extend away from the bone anchors 30. As shown, the cross-bar 34, the legs 38, and the vertebral body "V" together form a fixed trapezoidal shaped construct 42, the location and orientation of which can be controlled. Once the vertebral bodies "V" have been realigned, a fixation rod may be placed into the channels of the bone anchors 30 on either side of the spinous process to thereby stabilize the spine.

As shown in FIG. 2, each alignment device 18 further includes a first adjustment arm 46, and a second adjustment arm 50 that are each pivotal relative to the second ends of the legs 38. As shown, the first and second adjustment arms 46 and 50 may be pivotally coupled to the cross-bar 34 at a pivotal connection 52 that is spaced from the legs 38. The first and second adjustment arms 46 and 50 are also pivotally coupled to a respective one of the first side 22 and second side 26 of the frame 14. The adjustment arms 46 and 50 may be pivotally coupled at the pivotal connections 52 such that the adjustment arms 46 and 50 can pivot about respective first axes that extend in the first or caudal-cranial direction. Similarly, the adjustment arms 46 and 50 are coupled to the first and second sides 22 and 26 such that the adjustment arms 46 and 50 can pivot about respective second axes that also extend in the first or caudal-cranial direction. As shown, the second axes are defined by the sides 22 and 26. Each adjustment arm 46 and 50 is configured to be adjusted and also pivoted about the respective first or second sides 22 and 26 to thereby realign the vertebral body "V" with respect to the other vertebral bodies. It should be understood that the first adjustment arm 46, the second adjustment arm 50, or both adjustment arms 46 and 50 may be adjusted and/or pivoted to realign the vertebral body, depending on what movement is required to realign the vertebral body.

Figure 3C:
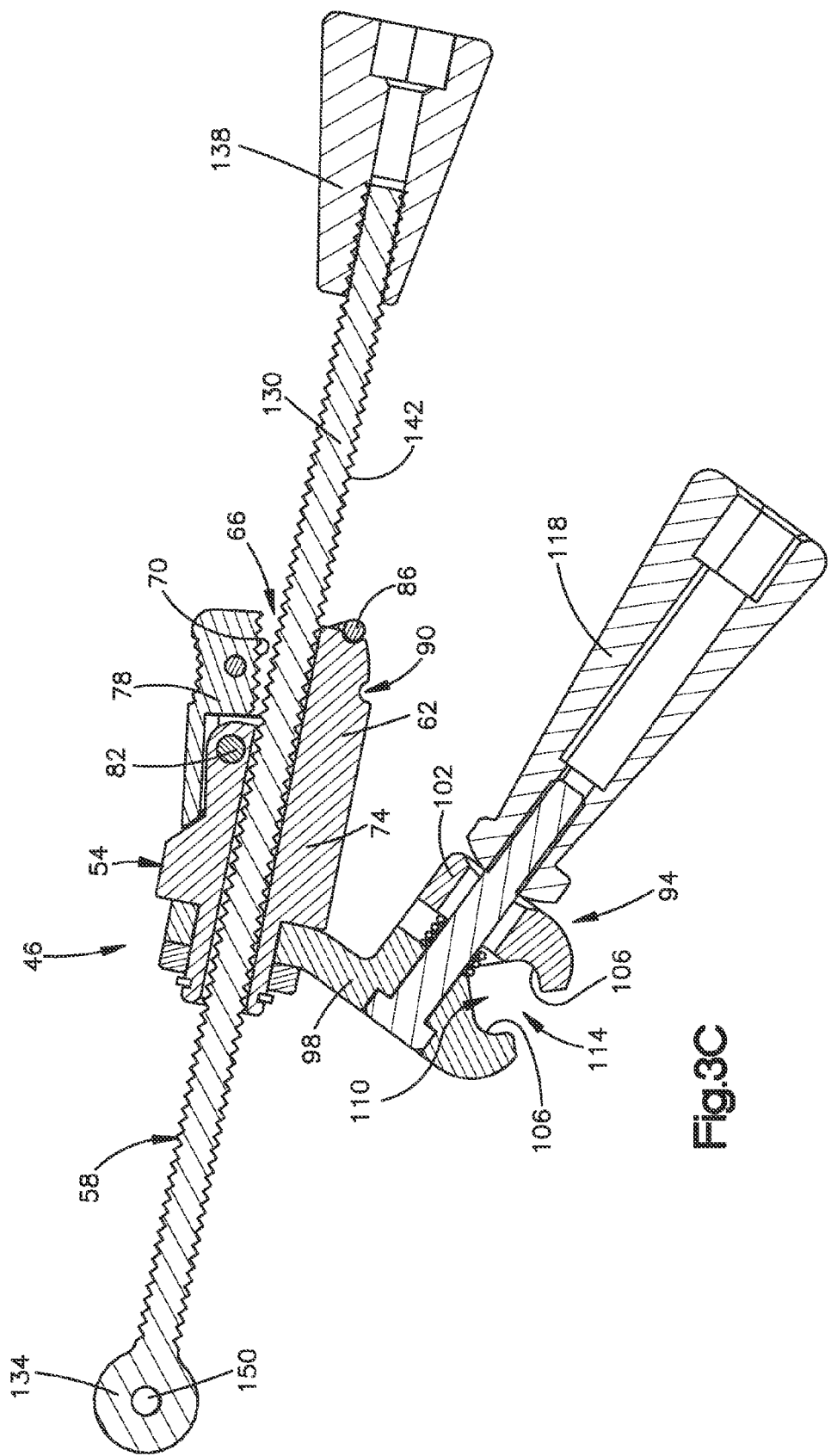
FIG. 3C is a sectional view of the adjustment arm shown in FIG. 3B.

Referring to FIGS. 3A-3C, the adjustment arms 46 and 50 are constructed identically and therefore it should be understood that while the first adjustment arm 46 will be described, the second adjustment arm 50 is constructed in a similar manner. Moreover, each adjustment arm 46 and 50 is capable of operating in the same manner regardless of what side of the frame 14 the arm is connected. It should be understood that each component of the first adjustment arm may later be referred to as a first component, and each component of the second adjustment arm may later be referred to as a second component even though the components will be described generally. As shown in FIG. 3A, the first adjustment arm 46 can include a medial housing 54, and an elongate member 58 that extends through the medial housing 54. The medial housing 54 is configured such that the elongate member 58 can translate through the medial housing 54, and subsequently be fixed in place. Therefore, the medial housing 54 may be disposed along any portion of the length of the elongate member 58. Additionally, the medial housing 54 is configured to pivotally couple the adjustment arm 46 to the first or second sides 22 and 26 of the frame 14.

As shown in FIGS. 3A-3C, the medial housing 54 can include a housing body 62 that defines a channel 66 extending therethrough. The channel 66 receives the elongate member 58 such that the elongate member 58 extends completely through the channel 66. As shown in FIG. 3C, the channel 66 carries an engagement member 70 that is configured to control the translation of the elongate member 58 within the channel 66. In the illustrated embodiment, the engagement member 70 is a thread that is configured to engage a thread defined by the elongate member 58. It should be understood, however, that the engagement member 70 may include other configurations, such as ridges, as desired.

As shown in FIGS. 3A and 3B, the housing body 62 can include a first body portion 74 and a second moveable body portion 78 that is coupled to the first body portion 74. As shown, the second moveable body portion 78 is rotatably coupled to the first body portion 74 by a pin 82, and is capable of being rotated between a first or closed position as shown in FIG. 3A, and a second or open position as shown in FIG. 3B. While in the closed position, the engagement member 70 is engaged with the elongate member 58, and while in the open position, the engagement member 70 is disengaged from the elongate member 58 to thereby allow free translation of the elongate member 58 with respect to the medial housing 54.

As shown in FIG. 3C, the first body portion 74 and the moveable body portion 78 together define the channel 66. Only the portion of the channel 66 that is defined by the moveable portion 78, however, carries the engagement member 70. Therefore, when the moveable body portion 78 is in the open position, the elongate member 58 is free to translate with respect to the medial housing 54. As shown, the moveable body portion 78 may include a latch 86 that holds the moveable body portion 78 in the closed position. The latch 86 may extend below the first body portion 74 and engage a recess 90 defined by the first body portion 74 to thereby securely lock the moveable body portion 78 in the closed position.

As shown in FIG. 3A, the medial housing 54 further includes a clip 94 that is configured to attach the adjustment arm 46 to the frame 14 such that adjustment arm can pivot about an axis defined by the side 22 or 26 of the frame 14 to which it is attached. As shown, the clip 94 includes a stationary arm 98 that extends down from the first body portion 74 and a clamping portion 102 that is rotatably coupled to the stationary arm 98. As shown in FIG. 3C, when in use the stationary arm 98 extends down and then angles laterally toward the legs 38. Both the stationary arm 98 and the clamping portion 102 define opposed concave recessed portions 106 that together define a frame channel 110 that is configured to receive the side of the frame 14. As shown, the frame channel 110 has an opening 114 that allows the side of the frame 14 to be received within the frame channel 110. Because of the angled stationary arm 98, the clip 94 may be attached to the frame from a partial lateral approach. To enlarge the opening 114, a handle 118 extends out from the clamping portion 102. While the opening 114 is enlarged, the side 22 or 26 may be received within the channel 110. Once received, the handle 118 may be partially tightened and the opening 114 reduced so as to clamp the adjustment arm to the frame 14. At least initially, the clamping force may be sufficient to couple the adjustment arm to the frame 14, while at the same time allowing the adjustment arm to pivot about the axis defined by the side 22 or 26 of the frame 14. Once the adjustment arm has pivoted and the vertebral body has been moved the clip 94 may be fully tightened to fixedly couple the adjustment arm 46 to the side of the frame 14.

With continued reference to FIGS. 3A-3C, the elongate member 58 includes a rod 130, a joint 134 at a distal end of the rod 130, and a handle 138 at a proximal end of the rod 130. The rod 130 is elongate and extends completely through the channel 66 of the medial housing 54. The rod 130 carries an engagement member 142 that is configured to engage the engagement member 70 of the medial housing 54. In the illustrated embodiment, the engagement member 142 is a thread that is configured to engage the thread defined by the medial housing 54. Therefore, when the moveable body portion 78 of the medial housing 54 is in the closed position, and the engagement members 70 and 142 are engaged, rotation of the elongate member 58 via the handle 138 will incrementally translate the elongate member 58 through the medial housing 54.

As shown in FIGS. 3A and 3C, the joint 134 of the elongate member 58 is a ball joint that is spherically shaped. It should be understood, however, that the joint 134 may have other configurations, as desired. As shown, the joint 134 defines a bore 150 that extends into the joint 134. In the illustrated embodiment, the bore 150 extends completely through the joint 134. The joint 134 is configured to be received by a socket that is defined by the cross-bar 34 such that the elongate member 58 can pivot about the joint 134. Therefore, the adjustment arms 46 and 50 can be pivotally coupled to both the frame 14 and to the cross-bar 34.

Now referring to FIGS. 4A-4C, the cross-bar 34 includes a first rail 160 and a second rail 164 that is parallel to and spaced apart from the first rail 160. The cross-bar 34 may be made from an electrically non-conductive material, such as Radel™ so that each bone anchor can be distinguished during neuromonitoring. As shown, the first and second rails 160 and 164 are spaced from each other such that a gap 168 is defined between the rails. The rails 160 and 164 are elongate in the medial lateral direction when in use and together define a joint 172 at opposed ends of the cross-bar 34. The joints 172 in the illustrated embodiment are sockets that are configured to receive the spherical joints 134 of the elongate members 58. In particular, the rails 160 and 164 define opposed inner concave recesses 176 that together define the socket. Initially, the gap 168 between the rails 160 and 164 is such that the joints 134 of the elongate members 58 can be received by the joints 172 of the cross-bar 34. Once the joints 134 and 172 have been mated, the gap 168 between the rails 160 and 164 may be reduced to thereby secure the adjustment arms 46 and 50 to the cross-bar 34 such that the adjustment arms 46 and 50 are pivotally coupled to the cross-bar 34. By having a spherical joint, the elongate members 58 may be capable of pivoting in multiple planes. The joints may also be configured as a cylindrical joint. For example, the cross-bar 34 may include locking pins 178 that are configured to extend through the rails 160 and 164 and engage the bores 150 of the spherical joints 134 to thereby limit the pivot or rotation to a single plane. When the pins 178 are placed, rotation of the medial housings 54 may adjust the adjustment arms 46 and 50 when the engagement members 70 of the moveable portions 78 are engaged with the engagement members 142 of the elongate members 58. It should be understood, however, that the joints may be located anywhere along the cross-bar 34, and that the joints may have any configuration, so long as the adjustment arms 46 and 50 are pivotal with respect to the cross-bar 34.

To reduce the gap 168 between the rails 160 and 164, the cross-bar 34 further includes a locking element 180 proximate to each joint 172. As shown, the locking element 180 may be a threaded bolt that draws the rails 160 and 164 closer to each other by rotating the locking elements 180. It should be understood, that the gap 168 may be reduced in other ways. For example, the rails 160 and 164 may be flexible and may flex outward to receive the joints 134 and then return to their original orientation to retain the joints 134.

As shown in FIG. 4C, each rail defines a laterally elongate slot 200 that extends longitudinally through the rail. In the illustrated embodiment the slots 200 each define a first slot portion 204 and a second slot portion 208 that is laterally separated from the first slot portion 204. It should be understood, however, that the first and second slot portions 204 and 208 may be joined to define a single continuous slot. As shown, the first slot portions 204 of the first and second rails 160 and 164 are aligned in the longitudinal direction, and the second slot portions 208 are aligned in the longitudinal direction. The slots 200 are configured to receive locking mechanisms so that the legs 38 can be coupled to the cross-bar 34 at various positions along the lateral length of the cross-bar 34.

As shown in FIGS. 4B and 4C the outer surfaces of the rails 160 and 164 define engagement features 212. In the illustrated embodiment, the engagement features 212 are teeth or ridges that are disposed above and below the slots 200. As will be described, the engagement features 212 help lock the legs 38 to the cross-bar 34. It should be understood, that the engagement features 212 may include other configurations, as desired, or alternatively, the rails 160 and 164 can be devoid of engagement features 212.

Figure 5A:
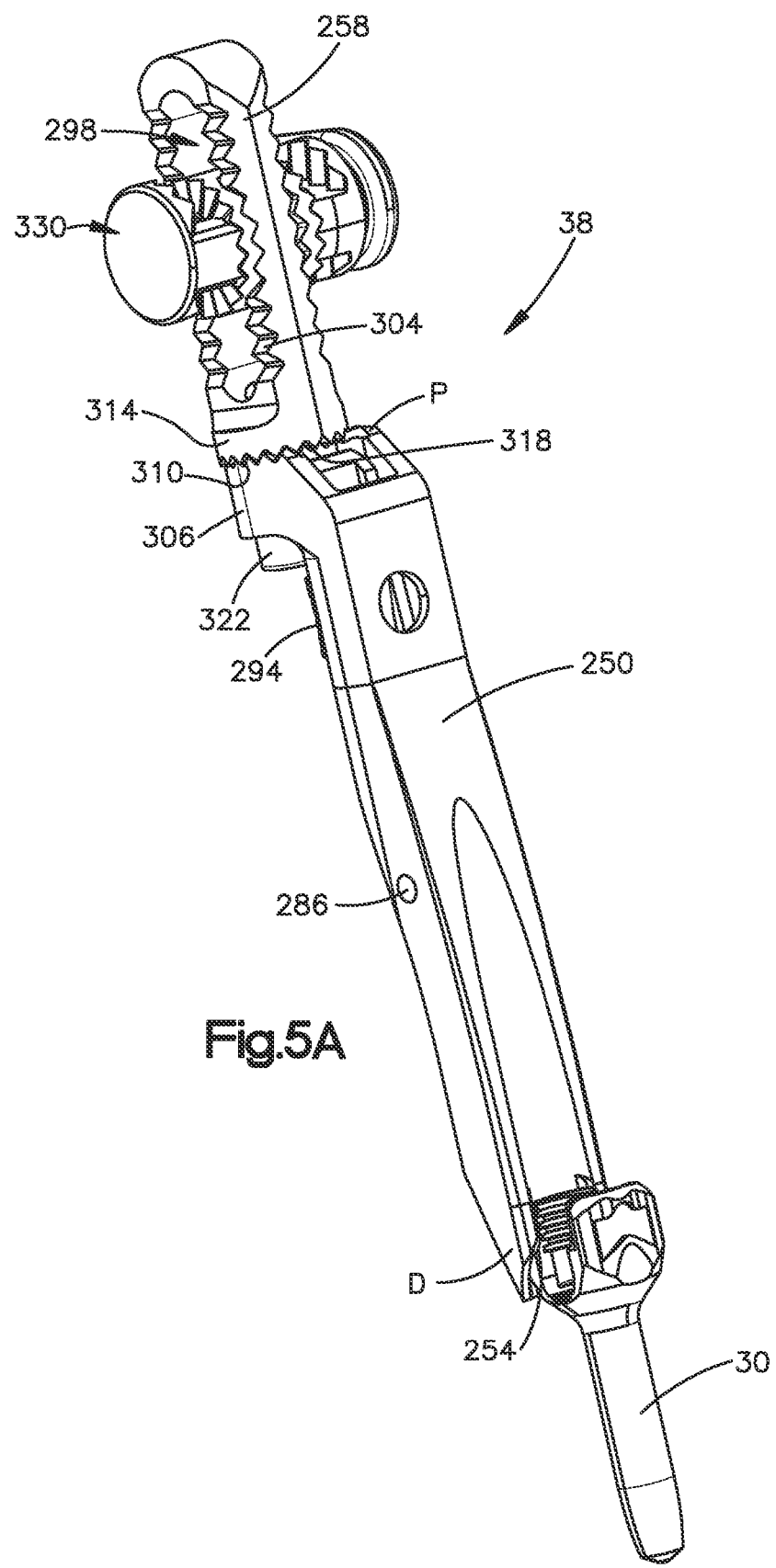
FIG. 5A is a perspective view of one of the legs shown in FIG. 2.

As shown in FIGS. 5A-5C, the legs 38 may be fixedly coupled to the cross-bar 34 and to a respective bone anchor 30. The legs 38 are constructed identically and therefore it should be understood that while one leg 38 will be described, the other leg 38 is constructed in a similar manner. As shown in FIG. 5A, each leg 38 includes an elongate body 250 that defines a distal end "D" and a proximal end "P". The leg 38 further includes a bone anchor coupler 254 that extends distally from the distal end of the elongate body 250, and cross-bar coupler 258 that extends proximally from the proximal end of the elongate body 250. As shown in FIG. 5B, the bone anchor coupler 254 may define a recess 262 that is configured to receive the head of the bone anchor 30 in a snap fit connection. It should be understood, however, that the bone anchor coupler 254 may include other configurations. For example, the bone anchor coupler 254 may define a head having external threads that can be threaded into the head of the bone anchor 30.

As shown in FIG. 5B, the leg 38 may also include a release mechanism 270 that is configured to release or otherwise disengage the leg 38 from the bone anchor 30. As shown, the release mechanism 270 includes a lever 274 that extends within a cavity 278 defined by the elongate body 250. A distal end of the lever 274 defines a lip 282 that engages the bone anchor 30 when the leg 38 is fixedly coupled to the bone anchor 30. The lever 274 is pivotally coupled to the elongate body 250 by a pin 286. A proximal end of the lever 274 defines a recess 288 that receives a leaf spring 292 that keeps tension between the lever 274 and the bone anchor 30. The release mechanism 270 further includes a press button 294 that is coupled to the leaf spring 292, such that when the press button 294 is pressed, the lever 274 rotates about pin 286 and the lip 282 disengages from the bone anchor 30 thereby releasing the leg 38 from the bone anchor 30.

As shown in FIGS. 5A and 5B, the cross-bar coupler 258 of the leg 38 may be oriented to be received within the gap 168 of the cross-bar 34. As shown, cross-bar coupler 258 is a substantially rectangular shaped component that defines a slot 298 extending longitudinally therethrough. The slot 298 is elongate in the transverse direction and is configured to align with the slots 200 of the cross-bar 34. In particular, the cross-bar coupler 258 is disposed within the gap 168 between the rails 160 and 164 such that the slot 298 and the slots 200 align to thereby define a through hole. Because the slot 298 is elongate in the transverse direction, the cross-bar 34 can be moved toward or further away from the vertebral body and the slots 200 and 298 will still align to define the through hole. Therefore, the distance between the cross-bar 34 and the vertebral body may be adjustable to accommodate various vertebral anatomies.

As shown in FIG. 5A, the cross-bar coupler 258 further includes engagement features 304, illustrated as teeth or ridges extending from its outer surfaces. The engagement features 304 may be configured to help fixedly couple the legs 38 to the cross-bar 34.

As shown in FIG. 5B, the cross-bar coupler 258 of the leg 38 may be adjustable or otherwise rotatable so that the coupler 258 can be oriented to be received within the gap 168 regardless of the orientation of the bone anchor 30. In that regard, the proximal end of the elongate body 250 defines a shelf 306 having radially extending ridges or teeth 310 extending from an outer surface of the shelf 306. The ridges 310 define a circular array, and the shelf 306 further defines a bore 308 extending transversely through the center of the circular array of ridges 310 of the shelf 306. Similarly, a distal end of the cross-bar coupler 258 defines a shelf 314 having radially extending ridges or teeth 318 that are configured to engage and mate with the ridges 310 of the elongate body 250. The cross-bar coupler 258 may be rotated about an axis defined by the leg 38 until a desired orientation is achieved. Once achieved, the cross-bar coupler 258 may be moved toward the elongate body 250 until the ridges 318 of the cross-bar coupler 258 engage the ridges 310 of the elongate body 250. A pin 322 may then be inserted through the bore 308 and into the cross-bar coupler 258 to thereby couple the cross-bar coupler 258 to the elongate body 250 in the desired orientation. The ridges 310 and 318 prevent the cross-bar coupler 258 from rotating after the orientation has been set. Such a configuration allows the legs 38 to be easily coupled to the cross-bar 34 regardless of the orientation of the bone anchors 30. It should be understood, however, that the cross-bar coupler 258 may be integrally formed with the elongate body 250. Moreover, the cross-bar coupler 258 may be disposed anywhere along the elongate body 250 so long as the cross-bar coupler 258 is proximate to the proximal end of the body 250.

As shown in FIGS. 5A-5C, each leg 38 further includes a locking mechanism 330 that extends through the through hole defined by the slots 200 and 298 to thereby fixedly couple the legs 38 to the cross-bar 34. As shown, the locking mechanisms 330 each include a rod 332 and a pair of toothed washers 334. Once the legs 38 have been properly positioned within the gap 168, the rod 332 may be inserted through the through hole and the teeth of the toothed washers 334 may engage the engagement features 212 defined by the cross-bar 34 to thereby fixedly couple the legs 38 to the cross-bar 34 in the desired angular orientation, as required by the orientation of the bone anchors 30.

In operation and in reference to FIGS. 6A and 6B, the alignment device 18 is coupled to the frame 14 and is configured to adjust the position of the vertebral body "V". Each leg 38 may be coupled to a respective bone anchor 30 such that the legs 38 extend posteriorly from the vertebral body. The cross-bar 34 may be fixedly coupled to the cross-bar couplers 258 of the legs 38 such that the legs 38, the cross-bar 34, and the vertebral body together define a rigid trapezoidal shaped construct. The adjustment arms 46 and 50 may then be clipped onto the first and second sides 22 and 26 of the frame 14 using the clips 94 such that the adjustment arms 46 and 50 may pivot about the first and second sides 22 and 26. The elongate members 58 may be adjusted so that the joints 134 of the adjustment arms 46 and 50 may then be coupled to the cross-bar 34 such that the adjustment arms 46 and 50 may pivot with respect to the cross-bar 34. The alignment device 18 may therefore resemble a classic four-bar linkage mechanism. That is, the trapezoidal shaped construct may be considered a "third link" of the four-bar linkage mechanism, where the frame 14 is the "fourth link," and the pair of adjustment arms 46 and 50 are the "first" and "second links". The third link can be spatially located by adjusting the length and angles of the first and second links. This process may be repeated for additional alignment devices 18 until every desired vertebral body is coupled to the frame 14 via a respective alignment device 18.

In one technique an alignment device 18 may be attached to two respective neutral vertebral bodies (i.e. non-deformed in spatial orientation) both above and below the deformed array of vertebral bodies. These four alignment devices 18 are configured in the central and fully locked positions at all adjustment points. These four alignment devices 18 create a foundation which supports the frame and "grounds" it to the patient's body. All subsequent alignment devices 18 may be attached to the frame 14 and to the deformed vertebral bodies. These subsequent alignment devices 18 may then re-position the deformed vertebral bodies relative to the grounded frame 14 and the neutral vertebral bodies. Supplemental fixation of the frame 14 to a hospital bed rail may also be performed depending on patient size, weight, and severity of deformity.

Once the system 10 is coupled to the vertebral bodies, the adjustment arms 46 and 50 may be further adjusted to translate the vertebral body along the second or lateral direction. For example, a first length $L_1$ defined between the first side 22 of the frame 14 and the second end of the first leg 38 may be adjusted by translating the engagement arm 58 relative to the medial housing 54. Similarly, a second length $L_2$ defined between the second side 26 of the frame 14 and the second end of the second leg 38 may be adjusted by translating the engagement arm 58 relative to the medial housing 54. Therefore, the lengths $L_1$ and $L_2$ may be reduced or extended, as desired. To translate or move the vertebral body, the moveable portion 78 of the medial housing 54 of the first adjustment arm 46 is in the open position to allow free translation of the elongate member 58 of the first adjustment arm 46, and then by either rotating, pulling, or pushing the elongate member 58 of the second adjustment arm 46, the vertebral body can be translated. It should be understood, however, that the vertebral body can also be translated or moved by rotating, pulling, or pushing the elongate member 58 of the first adjustment arm 46.

The vertebral bodies may also be moved by applying a moment or other force to the adjustment arms 46 and 50. The force will cause the adjustment arms 46 and 50 to pivot about the first and second sides 22 and 26 of the frame 14, respectively to thereby cause the vertebral body to rotate about a longitudinal axis that extends in the first or caudal-cranial direction and move in substantially the second and third directions. The vertebral body may rotate about the longitudinal axis without translating, may rotate about the longitudinal axis while at the same time translating in the third (anterior-posterior) or second (lateral-medial) directions, or the vertebral body may purely translate in only the third (anterior-posterior) direction, only the second (medial-lateral) direction or in some combination of the third (anterior-posterior) and second (medial-lateral) directions. This process may be repeated for each alignment device 18 until the vertebral bodies are properly aligned in the midline sagittal plane. Once aligned, the clips 94 of the adjustment arms 46 and 50 may be tightened so that the vertebral bodies are fixed in position. A fixation rod may then be coupled to the bone anchors 30 with a locking cap inserted through the gap 168 of the cross-bar 34 to thereby stabilize the spine, and the system 10 may be removed.

Figure 7:
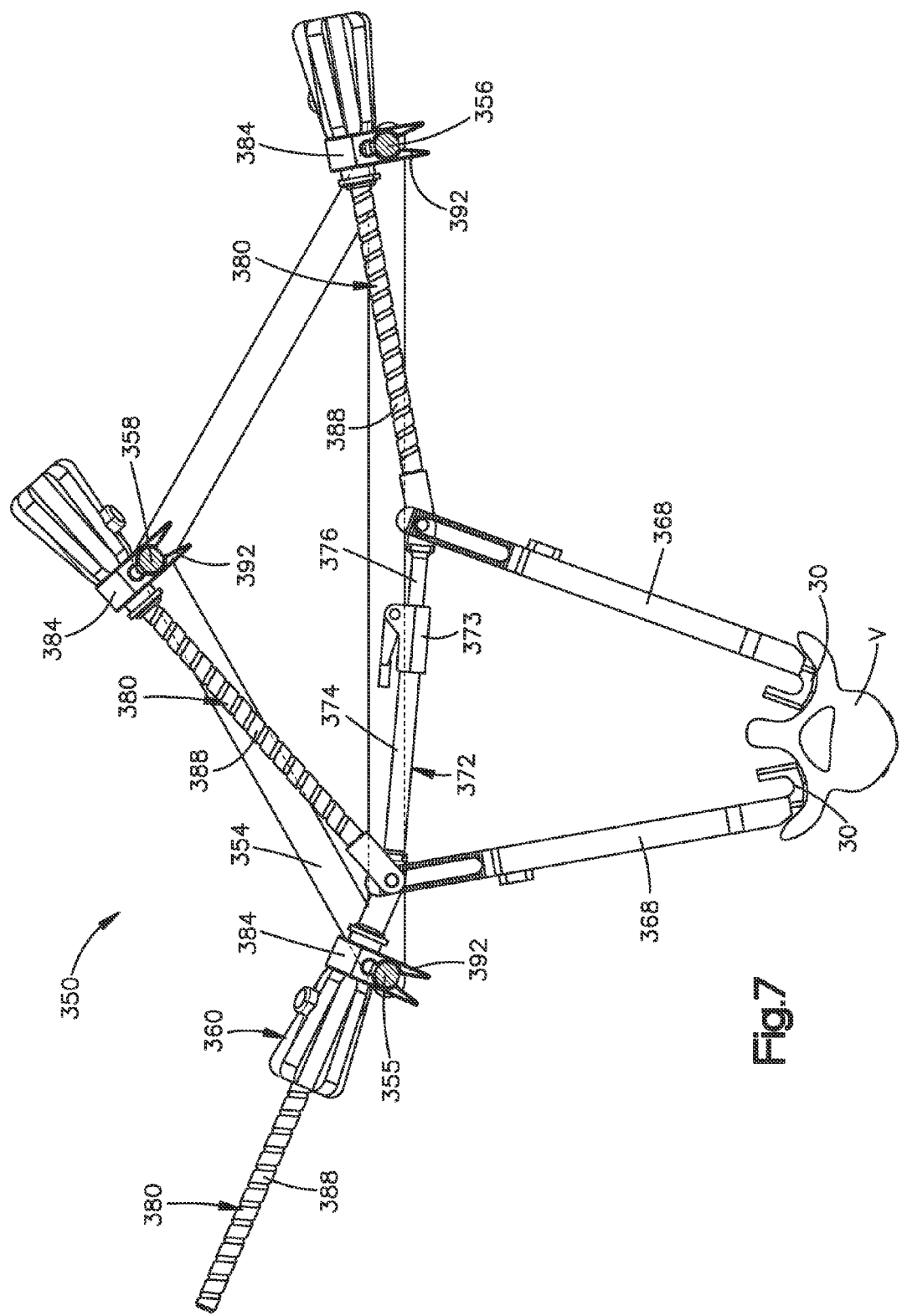
FIG. 7 is a side elevation view of an alignment system constructed in accordance with another embodiment, the alignment system includes a frame having three sides and three adjustment arms pivotally coupled to the sides.

In another embodiment and in reference to FIG. 7, a vertebral adjustment system 350 may include a frame 354 having a first side (i.e. rod) 355, a second side (i.e. rod) 356, and a third side (i.e. rod) 358. The first, second, and third sides 355, 356, and 358 extend parallel to each other and are spaced apart from each other so as to define an equilateral triangle. The adjustment system 350 may also include a plurality of alignment devices 360 that are coupled to the frame 354. The adjustment system 350 operates in a similar manner as the adjustment system 10, and therefore includes similar structure unless otherwise stated.

As shown in FIG. 7, each alignment device 360 includes a pair of legs 368 that extend from respective bone anchors 30, and a cross-bar 372 that is coupled to the legs 368. Together the legs 368, the cross-bar 372, and the vertebral body define a substantially trapezoidal shaped rigid construct 376 that can be moved.

The cross-bar 372 includes a clamp 373, a first elongate member 374, and a second elongate member 376 that is moveably coupled to the first elongate member 374 by the clamp 373. The second elongate member 376 can be adjusted to increase or decrease the lateral length of the cross-bar 372. Therefore, the cross-bar 372 can be adjusted to be coupled to the legs 368 after the legs have been coupled to the bone anchors.

As shown in FIG. 7, the adjustment system 350 further includes first, second, and third adjustment arms 380 that are coupled to a respective first, second, and third side 355, 356, and 358 of the frame 354, and pivotally coupled relative to the legs 368. As shown, the adjustment arms 380 are pivotally coupled to the cross-bar 372. By having three adjustment arms 380 the adjustment arms 380 may be more securely coupled to the frame 354.

The adjustment arms 380 are constructed similar to each other, and operate in a similar manner as the adjustment arms 46 and 50 described above. As shown, each adjustment arm includes a medial housing 384 and an elongate member 388 that extends through the medial housing 384. Similar to the adjustment arms 46 and 50, the elongate members 388 are configured to translate through the medial housings 384 so as to adjust a length between the sides of the frame 354 and the second ends of the legs 368. As shown, the medial housings 384 may include a clip 392 that snaps onto the sides 355, 356, and 358 of the frame 354. Because there are three adjustment arms 380, the clips 392 don't have to be tightened after the vertebral bodies have been moved.

Similar to the adjustment system 10, the adjustment 350 may move the vertebral bodies by translating the elongate members 388 through the medial housings 384 by rotating the knob 360, or by applying a moment to the adjustment arms 380 to thereby rotate the arms 380 about the respective sides of the frame 354. Therefore, the vertebral body may be translated in the second direction, third direction, or some combination of the second and third directions. Moreover, the vertebral body may be rotated, as desired. Once the vertebral bodies have been realigned, a fixation rod may be coupled to the bone anchors on either side of the spinous processes of the vertebral bodies.

Figure 8:
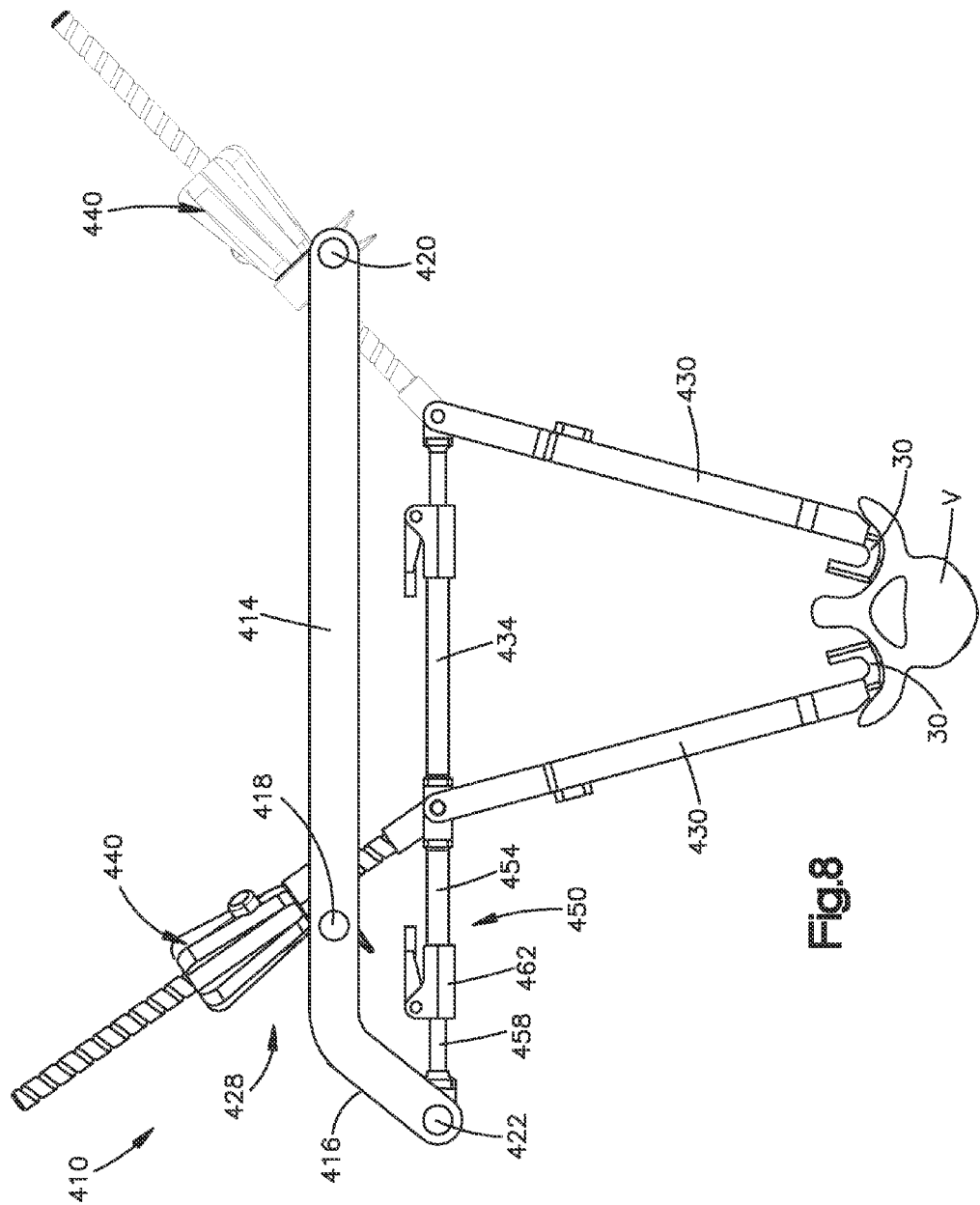
FIG. 8 is a side elevation view of an alignment system constructed in accordance with another embodiment, the alignment system includes a substantially L-shaped frame.

In another embodiment and in reference to FIG. 8, an adjustment system 410 may include a frame 414 that includes an angled portion 416 that supports a third side or rod. As shown, the frame 414 includes first, second, and third sides (i.e. rod) 418, 420, and 422, respectively. The sides 418, 420, and 422 extend parallel to each other, with the third side being located laterally and anteriorly to the first and second rods 418 and 420. The adjustment system 410 is constructed similar to and operates in a similar manner to the adjustment system 350 unless otherwise stated.

As shown, the system 410 includes a plurality of alignment devices 428, each of which includes a pair of legs 430 extending from the bone anchors 30, and a cross-bar 434 coupled to the legs 430. The alignment devices 428 further include first and second adjustment arms 440 that are coupled to the first and second sides 418 and 420 of the frame 414, and pivotally coupled relative to the legs 430. As shown, the first and second adjustment arms 440 are pivotally coupled to the cross-bar 434.

As shown in FIG. 8, each alignment device 428 further includes a third adjustment arm 450 that is pivotally coupled to both the third side 422 of the frame 414 and to the cross-bar 434. The third adjustment arm 450 includes a first member 454 and a second member 458 that is moveable relative to the first member 454. The third adjustment arm 450 may further include a clamp 462 that couples the first member 454 to the second member 458 and selectably fixes the second member 458 relative to the first member 454. The third adjustment arm 450 will lock the position of the vertebral bodies as the first and second adjustment arms 440 are adjusted and pivoted to the desired location, when clamp 462 is engaged.

In another embodiment and in reference to FIGS. 9A and 9B, an alignment system 510 is configured to manipulate the alignment of the vertebral bodies "V" of the spine "S" within different planes so as to realign them into a desired orientation. As shown, the alignment system 510 includes a frame 514, a main axial member 516 coupled to the frame 514, and at least one, such as a plurality of alignment devices 518 that are coupled to the main axial member 516. Each alignment device 518 is affixed to a respective vertebral body "V" so as to allow alignment of individual vertebral bodies "V" relative to the other vertebral bodies "V". The frame 514 may be constructed in the shape of a rectangle such that a first side 522 and an opposed second side 526 of the frame 514 provide substantially parallel members for connection of the main axial member 516. Each alignment device 518 is coupled to a respective pair of bone anchors 30, which are illustrated as pedicle screws that have been implanted into the vertebral bodies "V". The frame 514 is typically connected to an external frame such as a bed frame, but in some circumstances, may not be. The frame 514 is placed over the spine such that the first and second sides 522 and 526 extend laterally and are transverse to the spine. The main axial member 516 is coupled to the frame 514 such that the main axial member 516 extends in substantially the first or longitudinal or caudal-cranial direction between the first and second sides 522 and 526 and is disposed posterior to or otherwise adjacent the spine. For example, the main axial member 516 may extend within the midline sagittal plane. With proper positioning of the frame 514 and main axial member 516, the vertebral bodies may each have a respective alignment device 518 attached to it and the main axial member 516. The frame 514, the main axial member 516, and the alignment devices 518 may be constructed of stainless steel, titanium, CoCrM, carbon fiber, or other appropriate materials. As shown in FIG. 9B, and as will be described in more detail below, the vertebral bodies "V" may be aligned (e.g. rotated, moved laterally or medially, anteriorly or posteriorly, and caudally or cranially) via various movements of the alignment devices 518.

As shown in FIG. 10, each alignment device 518 can include a cross-bar 534, and a pair of legs 538 that are coupled to the cross-bar 534 and to respective bone anchors 30 that are implanted into the vertebral body "V". Legs 538 are coupled to, and extend from the bone anchors 30 in a similar manner as legs 38 shown in FIG. 2. The legs 538 are also coupled to the cross-bar 534 such that the cross-bar 534, the legs 538, and the vertebral body "V" together form a fixed trapezoidal shaped construct 542, the location and orientation of which can be controlled. Once the vertebral bodies "V" have been realigned, a fixation rod may be placed into the channels of the bone anchors 30 on either side of the spinous process to thereby stabilize the spine.

As shown in FIG. 10, each alignment device 518 further includes an adjustment mechanism 546 that is coupled to both the cross-bar 534 and the main axial member 516. In particular, the adjustment mechanism 546 is coupled to the main axial member 516 such that the entire alignment device 518 is capable of translating along the main axial member 516 along a first direction, and is coupled to the cross-bar 534 such that the cross-bar 534 is capable of translating through the adjustment mechanism 546 substantially along a second direction that is transverse to the first direction to thereby realign the vertebral body "V" with respect to the other vertebral bodies. Additionally, the adjustment mechanism 546 may be configured to translate the vertebral body in a third direction relative to the main axial member 516 and the other vertebral bodies. It should be understood, that the adjustment mechanism 546 may be configured to translate the vertebral body within a respective vertical plane, horizontal plane and/or a transverse plane.

Figure 11:
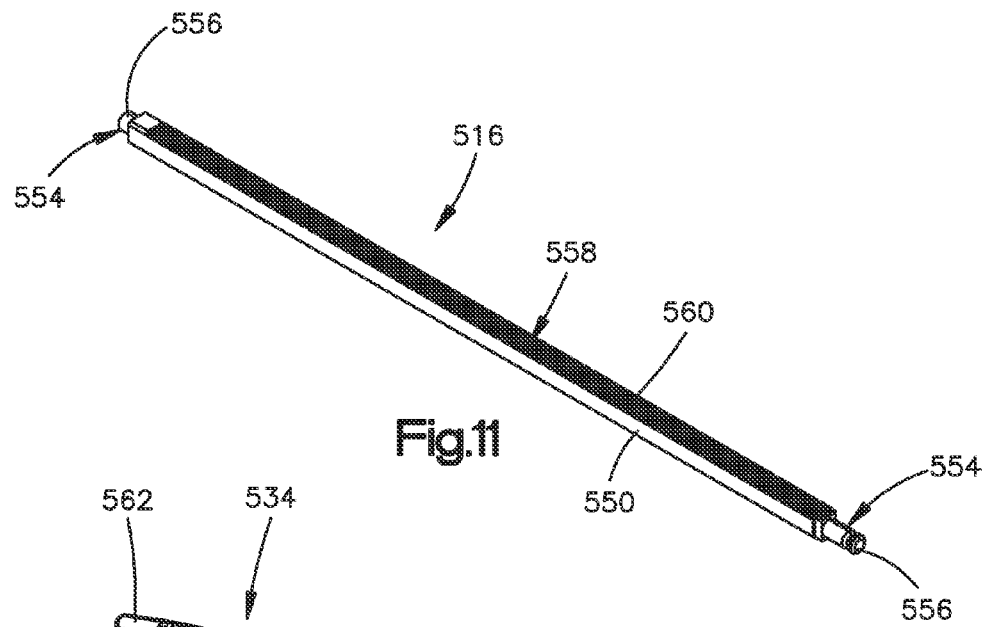
FIG. 11 is a perspective view of the main axial member shown in FIG. 10.

As shown in FIG. 11, the main axial member 516 includes a main member body 550 that is elongate in the longitudinal direction L, and a coupler 554 that extends from opposed ends of the main member body 550. The couplers 554 are illustrated as longitudinally elongate pegs 556 that are configured to engage the first and second sides 522 and 526 of the frame 514 in a snap fit connection so as to fixedly couple the main axial member 516 to the frame 514. It should be understood, however, that the couplers 554 may have other configurations capable of fixedly coupling the main axial member 516 to the frame 514. For example, the couplers 554 may be clamps.

As shown in FIG. 10, the main axial member 516 further include at least one engagement member such as a plurality of engagement members 558 that extend from a surface of the main member body 550. In the illustrated embodiment, the engagement members 558 are external teeth 560 that extend from an upper surface of the main member body 550. The teeth 560 extend in the lateral direction and are transverse to the longitudinal length of the main member body 550. The teeth 560 are disposed along a substantial portion of the length of the main member body 550. The teeth 560 are configured to be engaged by a corresponding engagement member(s) of the adjustment mechanism 546 of each alignment device 518 such that each alignment device 518 is capable of translating along the first or longitudinal or caudal-cranial direction along the main axial member 516 independently of the other alignment devices 518. It should be understood, however, that the engagement members 558 may have other configurations and that they may extend from any surface of the main member body 550. For example, the engagement member 558 may extend from either of the side surfaces of the body 550, the bottom surface of the body 550, or the main axial member 516 may be cylindrical and the engagement member 558 may be a thread that extends around the main member body 550. It should also be understood that the main axial member 516 may be devoid of engagement members 558 in some embodiments.

Figure 12A:
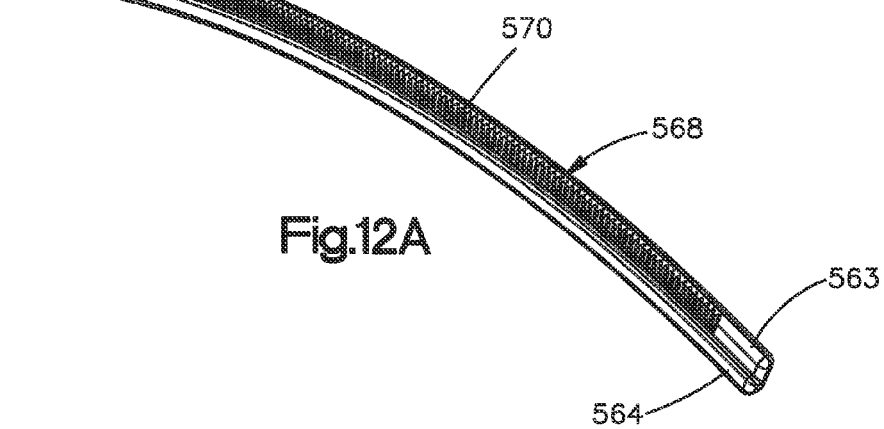
FIG. 12A is a perspective view of the cross-bar shown in FIG. 10.
Figure 12B:
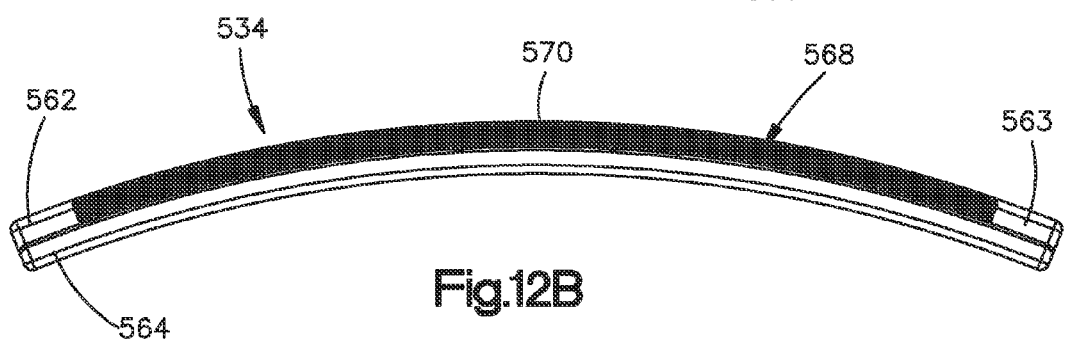
FIG. 12B is a side elevation view of the cross-bar shown in FIG. 12A.

As shown in FIGS. 12A and 12B, the cross-bar 534 includes a rail 562 that is elongate in the second or lateral or medial lateral direction when in use. As shown, the cross-bar 534 or at least the rail 562 is arched as it extends in the medial lateral direction. The arched profile of the cross-bar 534 allows the cross-bar 534 to follow an arched path as it translates through the adjustment mechanism 546 and the vertebral body that it is attached, to rotate within a transverse plane as the cross-bar 534 translates through the adjustment mechanism 546. The rail 562 may be L-shaped and include a transverse portion 563 and a ridge portion 564 that extends longitudinally from the transverse portion 563. As shown in FIG. 12A, the cross-bar further includes at least one engagement member such as a plurality of engagement members 568 that extend from a surface of the rail 562. In the illustrated embodiment, the engagement members 568 are external teeth 570 that extend from a side surface of the transverse portion 563. The teeth 570 extend in substantially the transverse direction and are transverse to the medial lateral elongate length of the rail 562. The teeth 570 are disposed along a substantial portion of the lateral length of the rail 562 and are configured to be engaged by a corresponding engagement member(s) of the adjustment mechanism 546 such that the cross-bar 534 is capable of translating through the adjustment mechanism 546. It should be understood, however, that the engagement members 568 may have other configurations and that they may extend from any surface of the rail 562. For example, the engagement members 558 may be threads that extend about the rail 562, and the engagement members 568 may extend from either of the side surfaces of the rail 562, the bottom surface of the rail 562, the top surface of the rail 562, or the cross-bar 534 may be cylindrical and the engagement member 568 may extend around the rail 562. It should also be understood that the cross-bar 534 may be devoid of engagement members 568 in some embodiments.

As shown in FIG. 12A, the ridge portion 564 extends longitudinally from the transverse portion 563 below the engagement members 568. The ridge portion 564 may help couple the legs 538 to the cross-bar 534. It should be understood, however, that the ridge portion 564 may extend from the transverse portion 563 above the engagement members 568 or the rail 562 may be devoid of the ridge portion 564.

Figure 13A:
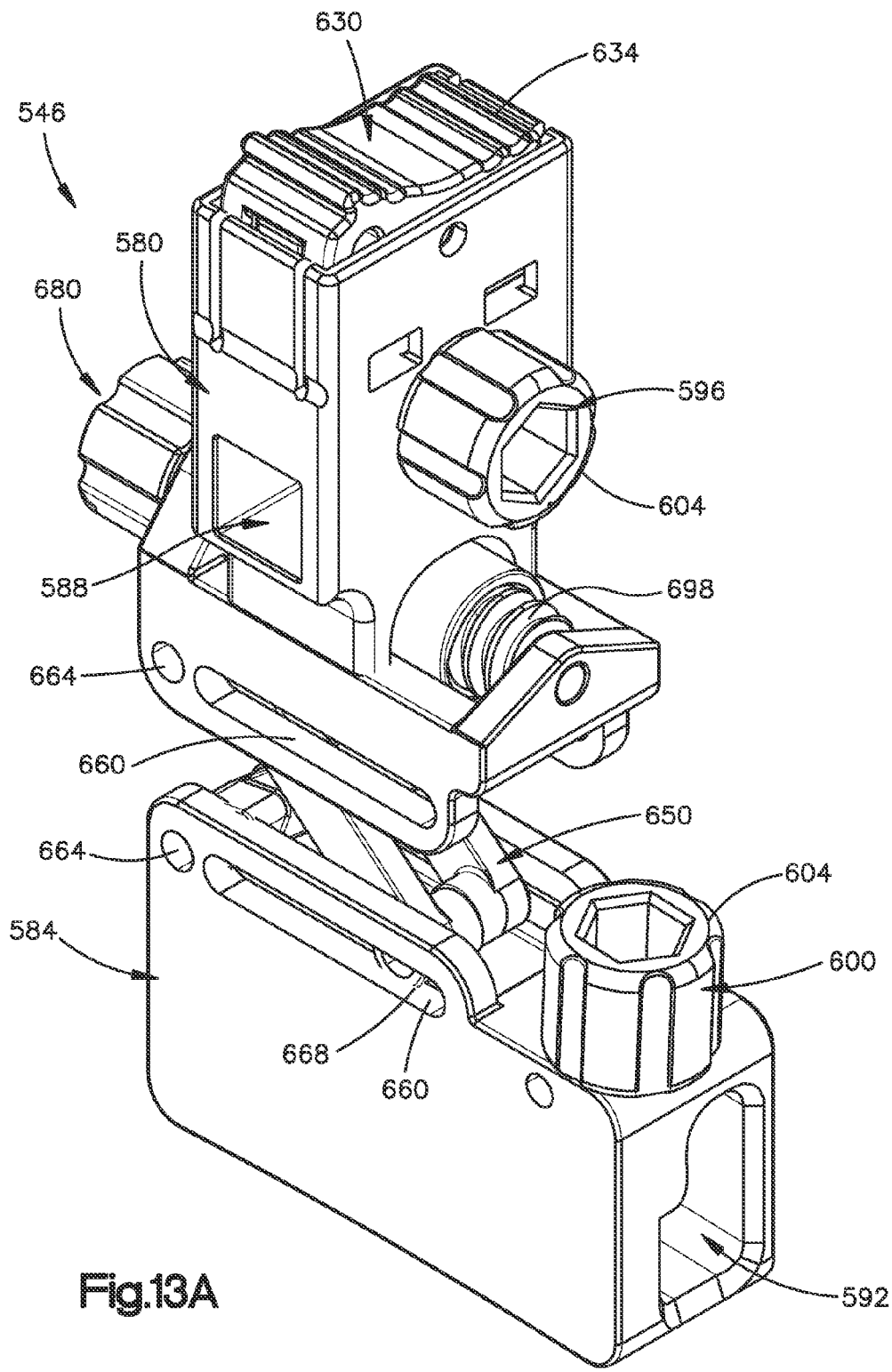
FIG. 13A is a perspective view of the adjustment mechanism shown in FIG. 10.

As shown in FIGS. 13A-13D, the adjustment mechanism 546 is configured to manipulate or otherwise cause the vertebral body to move relative to the other vertebral bodies. As shown in FIG. 13A, the adjustment mechanism 534 includes a first housing 580, and a second housing 584 that is coupled to and moveable relative to the first housing 580. As shown, the adjustment mechanism 534 defines a first channel 588 that extends through the first housing 580, and a second channel 592 that extends through the second housing 584. The first channel 588 extends in substantially the first or longitudinal direction and is configured to receive the main axial member 516. The second channel 592 extends in substantially the second or lateral direction and is transverse to the first channel 588. The second channel 592 is configured to receive the cross-bar 534 such that the cross-bar 534 can be selectively translated through the second channel 592.

Figure 13B:
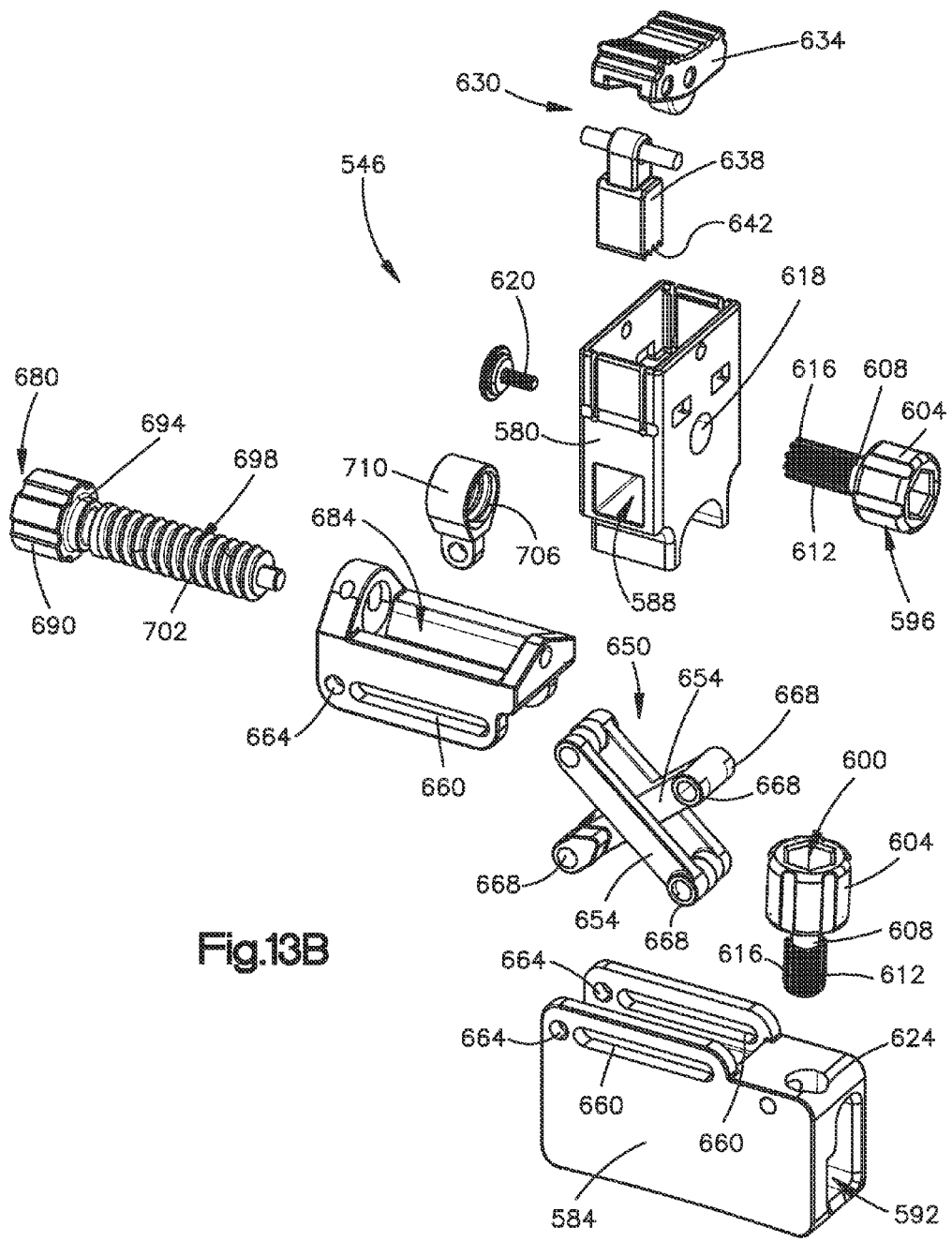
FIG. 13B is an exploded view of the adjustment mechanism shown in FIG. 13A, the adjustment mechanism includes a first housing, a second housing coupled to the first housing, a first adjustment knob extending into a first channel defined by the first housing, and a second adjustment knob extending into a second channel defined by the second housing.
Figure 13C:
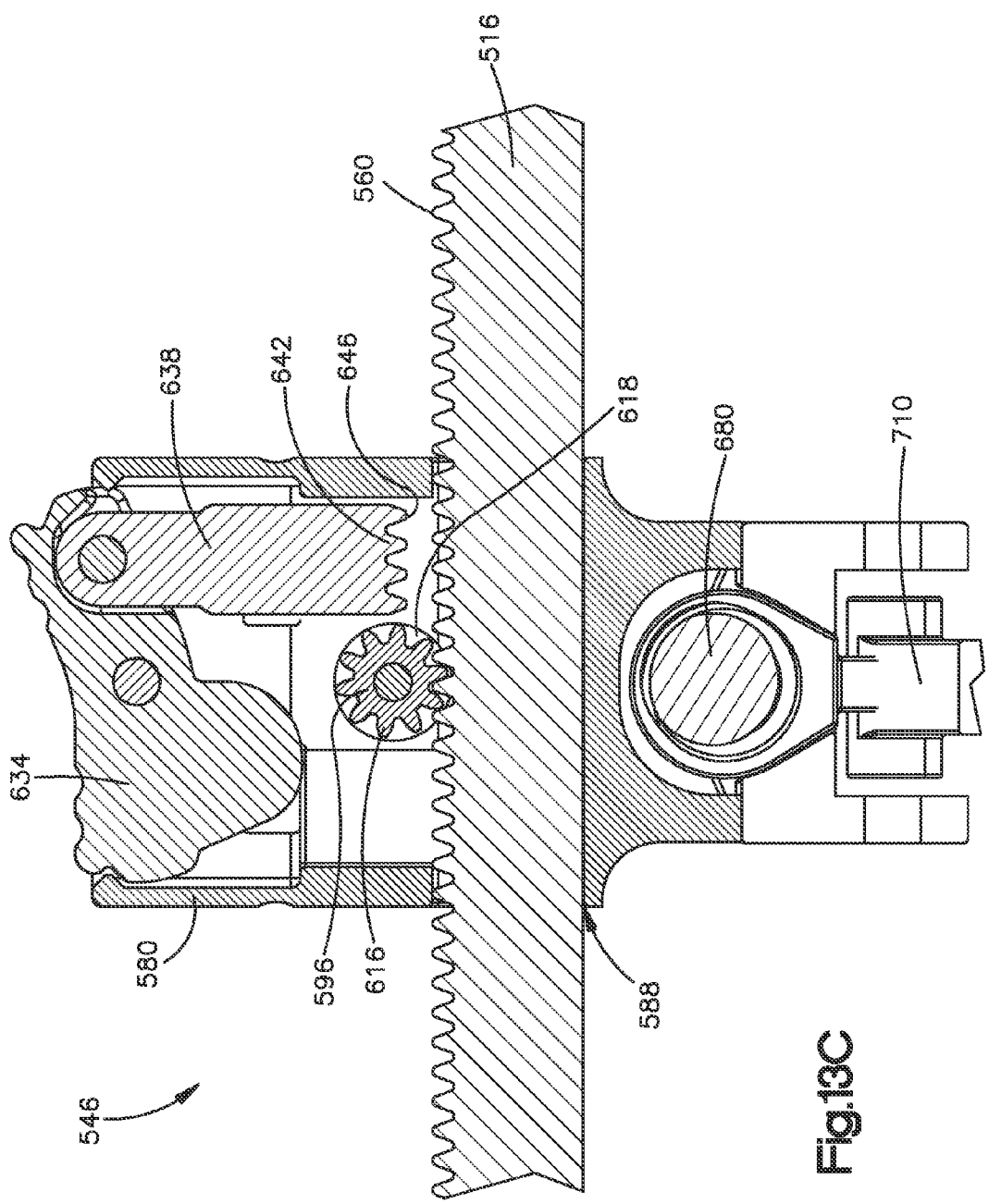
FIG. 13C is a cross-sectional view showing the first adjustment knob engaging the main axial member.

As shown in FIGS. 13A and 13B, the adjustment mechanism 546 further includes a first adjustment knob 596 that extends into the first channel 588, and a second adjustment knob 600 that extends into the second channel 592. As shown in FIG. 13B, the first and second adjustment knobs 596 and 600 each include a knob 604 and a cylindrical member 608 that extends from the knob 604. Each adjustment knob 596 and 600 further includes at least one such as a plurality of engagement members 612 that extend from the cylindrical member 608. In the illustrated embodiment the engagement members 612 are teeth 616 that are configured to engage corresponding teeth of the main axial member 516 or cross-bar 534. As shown in FIGS. 13B and 13C, the cylindrical member 608 of the first adjustment knob 596 extends through a bore 618 defined by the first housing 580 and into the first channel 588. The first adjustment knob 596 is fixedly coupled to the first housing 580 by a fastener 620. The teeth 616 of the first adjustment knob 596 engage the teeth 560 of the main axial member 516 such that rotation of the first adjustment knob 596 selectively or otherwise incrementally translates the alignment device 518 and thus the vertebral body along the main axial member 516. Therefore, the alignment device 518 and the vertebral body that is attached to the alignment device can move in the first or longitudinal or caudal-cranial direction.

Figure 13D:
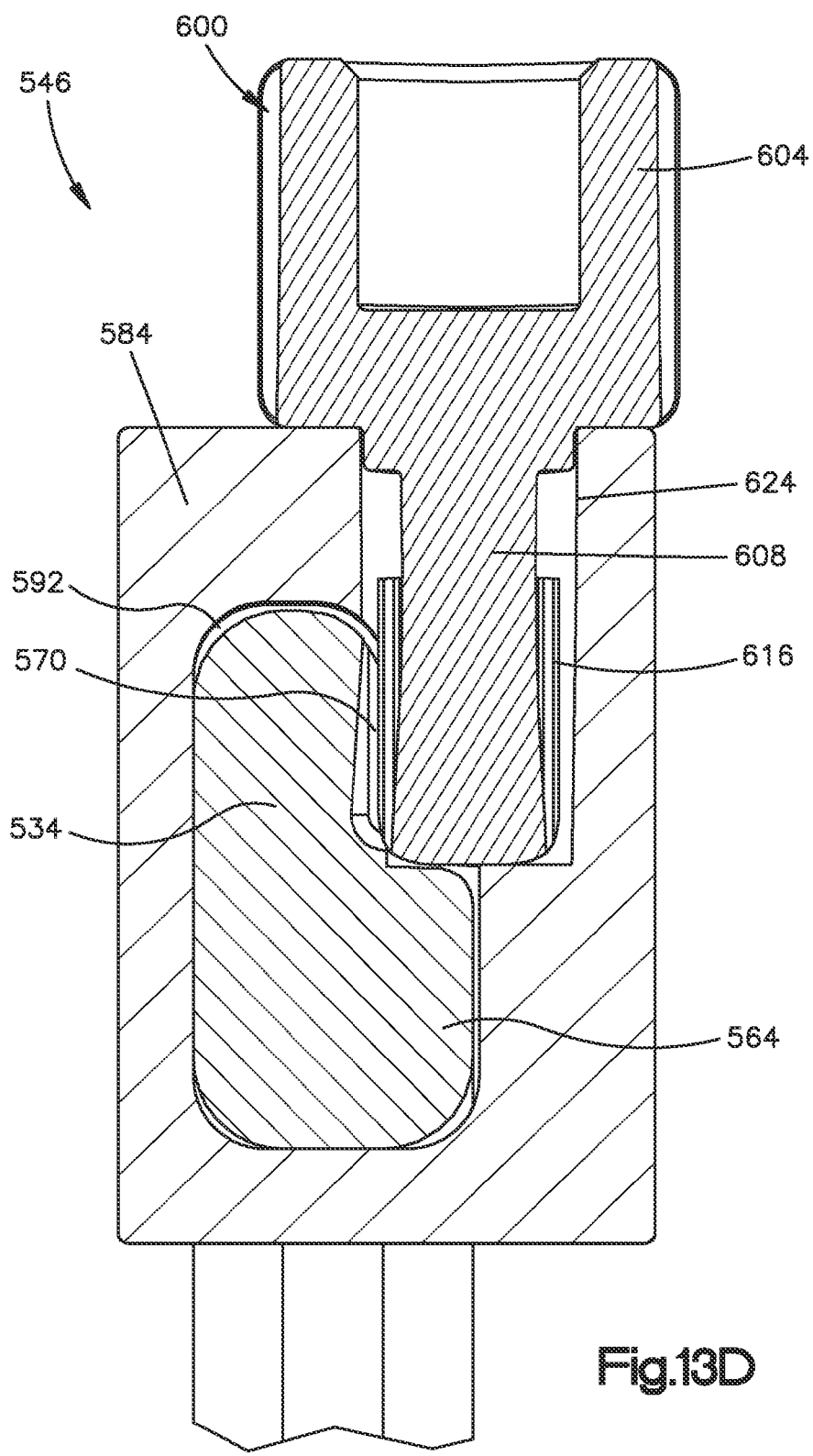
FIG. 13D is a cross-sectional view showing the second adjustment knob engaging the cross-bar.

Referring to FIGS. 13B and 13D, the cylindrical member 608 of the second adjustment knob 600 extends through a bore 624 defined by the second housing 584 and into the second channel 592. The teeth 616 of the second adjustment knob 600 engage the teeth 570 of the cross-bar 534 such that rotation of the second adjustment knob 600 selectively or otherwise incrementally translates the cross-bar 534 through the second channel 592. Therefore, the cross-bar 534 and the vertebral body that is attached to the cross-bar 534 via the legs 538 can move in the second, or lateral, or medial-lateral direction. Also, because the cross-bar 534 is arched, the vertebral body will be rotated within a transverse plane as the cross-bar 534 translates through the second channel 592.

Referring back to FIGS. 13B and 13C, the adjustment mechanism 546 further includes a lock 630 that is configured to lock the alignment device 518 in place once the alignment device 518 has been translated along the main axial member 516. As shown in FIG. 13B, the lock 630 includes a press button 634, a rotatable member 638 extending from the button, and an engagement member 642 extending from the rotatable member 638. As shown in FIG. 13C, the press button 634 is rotatably coupled to the first housing 580 such that the press button 634 can be pressed clockwise into a locked position or counterclockwise into an unlocked position. The rotatable member 638 is rotatably coupled to the press button 634 such that as the press button 634 is pressed clockwise or counterclockwise, the rotatable member 638 remains oriented in the same direction. As shown in FIG. 13C, the engagement member 642 can be a plurality of teeth 646 that are configured to engage the teeth 560 of the axial member 516. When the press button 634 is pressed into the locked position, the teeth 646 engage the teeth 560 of the main axial member 516 to thereby prevent further movement of the alignment device 518 along the main axial member 516.

As shown in FIGS. 13A and 13B, the second housing 584 is moveable relative to the first housing 580. As shown, the adjustment mechanism 534 can further include a linkage 650 that couples the first housing 580 to the second housing 584. As shown, the linkage 650 can include first and second crossed members 654. The bottom end of the first crossed member 654 is rotatably coupled to the first housing 580, and the top end of the first crossed member 654 is slidably coupled to the second housing 584. Similarly, the bottom end of the second crossed member 654 is slidably coupled to the second housing 584, and the top end of the second crossed member 654 is rotatably coupled to the first housing 580. Therefore, the first and second housings 580 and 584 each define a pair of spaced apart lateral elongate slots 660, and a pair of spaced apart bores 664 positioned adjacent the slots 660. The first and second crossed members 654 each include longitudinally extending pegs 668 at their ends that engage the bores 664 and slots 660. Therefore, each crossed member 654 will rotate within its respective bores 664 and slide within its respective slots 660 as the second housing 584 is moved relative to the first housing 580.

To move the second housing 584, the adjustment mechanism 546 includes a third adjustment knob 680 that extends into a third channel 684 defined by the first housing 580 and is coupled to the linkage 650. As shown in FIG. 13B, the third adjustment knob 680 includes a knob 690 and a cylindrical member 694 that extends from the knob 690. The adjustment knob 690 further includes at least one engagement member 698 that extend from the cylindrical member 694. In the illustrated embodiment the engagement member 698 is an external thread 702 and defines a worm gear. The thread 702 is configured to engage corresponding internal thread 706 of a coupler 710 that is attached to one of the crossed members 654. As shown in FIG. 13B, the cylindrical member 694 of the third adjustment knob 680 extends through a bore 710 defined by the first housing 580. The thread 702 of the third adjustment knob 680 engages the thread 706 of the coupler 710 such that rotation of the third adjustment knob 680 selectively or otherwise incrementally translates the second housing 584 and thus the vertebral body toward or away from the first housing 580. Therefore, the alignment device 518 is configured to move or otherwise translate the vertebral body along substantially the third, or longitudinal or anterior-posterior direction.

Figure 14:
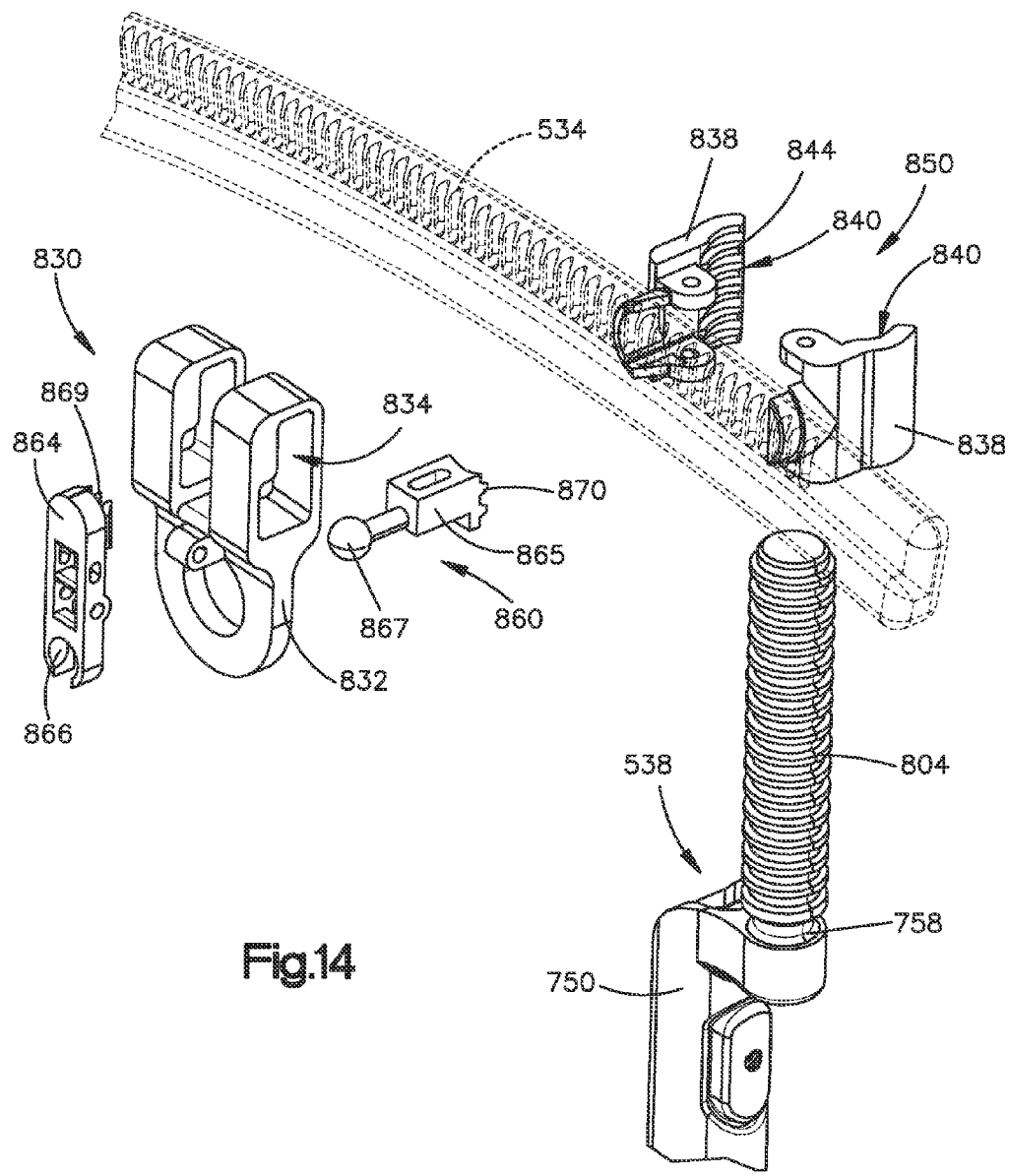
FIG. 14 is a partial exploded view of one of the legs being coupled to the cross-bar.

Now referring to FIGS. 10 and 14, the legs 538 are constructed similarly and operate in a similar manner as legs 538 described above unless otherwise stated. As shown in FIG. 14 each leg 538 may be fixedly coupled to the cross-bar 534 and to a respective bone anchor 30. As shown in FIG. 10, each leg 538 includes an elongate body 750, a bone anchor coupler 754 extending distally from the elongate body 750, and a cross-bar coupler 758 that extends proximally from the proximal end of the elongate body 750. The bone anchor coupler 754 is configured to receive the head of the bone anchor 30 in a snap fit connection. It should be understood, however, that the bone anchor coupler 754 may include other configurations. For example, the bone anchor coupler 754 may define a head having external threads that can be threaded into the head of the bone anchor 30.

The cross-bar coupler 758 of the leg 538 is a substantially cylindrical shaped component that extends in the transverse direction such that it is transverse to the lateral length of the cross-bar 534. As shown in FIG. 14, the cross-bar coupler 758 further includes engagement features 804, illustrated as ridges extending from the outer surface of the coupler 758. The engagement features 804 may be configured to help fixedly couple the legs 538 to the cross-bar 534.

As shown in FIG. 14, each leg 538 further includes a locking mechanism 830 that is configured to fixedly couple the legs 538 to the cross-bar 534. As shown, the locking mechanisms 830 each include a main body 832 that defines a laterally extending channel 834, and a pair of clamp members 838 that extend longitudinally from the main body 832. The channel 834 is configured to receive the cross-bar 534 such that the locking mechanism 830 can freely translate along the lateral length of the cross-bar 534. The clamp member 834 each define an opposed concave recess 840 and a plurality of engagement features 844 that extend out from the recesses 840. The recesses 840 together define a channel 850 that receives the cross-bar coupler 758. The engagement features 844 of the clamp members 838 engage the engagement features 804 of the cross-bar coupler 758 to thereby prevent transverse movement of the legs 538 relative to the cross-bar 534.

The locking mechanisms 830 further include a lock 860 that engages the engagement features 804 of the legs 538 to thereby prevent the locking mechanisms 830 and thus the legs 538 from translating along the lateral length of the cross-bar 534. As shown, the lock 830 includes a press button 864 coupled to the main body 832, and an engagement portion 865 coupled to the press button 864. The press button 864 is configured with a ball socket connection 866 on one end that connects with a ball 867 defined by the engagement portion 865. The press button 864 is further configured with teeth 869 at the other end that are configured to engage the teeth of the cross bar 534. The engagement portion 865 includes an engagement member 870 that is configured to selectively engage the teeth of the legs 538. Therefore, once the legs 538 have been positioned along the cross-bar 534 as desired, the press button 864 can be actuated so that the teeth 869 engages the cross-bar 534 to thereby fixedly couple the legs 538 to the cross-bar 534 in the desired position.

In operation and in reference to FIGS. 15A-15B, 16A-16B, and 17A-17B, the alignment device 518 is coupled to the main axial member 516 and is configured to adjust the position of the vertebral body "V". Each leg 538 may be coupled to a respective bone anchor 30 such that the legs 538 extend posteriorly from the vertebral body. The cross-bar 534 may be fixedly coupled to the cross-bar couplers 758 of the legs 538 such that the legs 538, the cross-bar 534, and the vertebral body together define a rigid trapezoidal shaped construct. The adjustment mechanism 546 at this point should be coupled to both the main axial member 516 and the cross-bar 534. This process may be repeated for additional alignment devices 518 until every desired vertebral body is coupled to the main axial member 516 via a respective alignment device 518.

Once the system 510 is coupled to the vertebral bodies, the adjustment mechanisms 546 may be activated to move the vertebral bodies along the first, second and/or third directions. For example, as shown in FIGS. 15A-15B, the second adjustment knob 600 may be rotated to thereby cause the cross-bar 534 and thus the vertebral body to which it is attached, to translate through the channel 592 relative to the main axial member 516 along the second or lateral direction. As shown in FIG. 15B, the vertebral bodies may all be realigned such that the vertebral bodies are aligned with the main axial member 516 within the midline sagittal plane.

As shown in FIGS. 16A-16B, the adjustment mechanism 546 may also be activated to move the vertebral bodies along the first or longitudinal direction. For example, the first adjustment knob 596 may be rotated to thereby cause the alignment device 518 to translate along the main axial member 516 in the first or longitudinal direction. As shown in FIG. 16B, the vertebral bodies may be moved to distract or contract the vertebral bodies away or toward adjacent vertebral bodies to properly space the vertebral bodies apart from each other as desired.

Figure 17A:
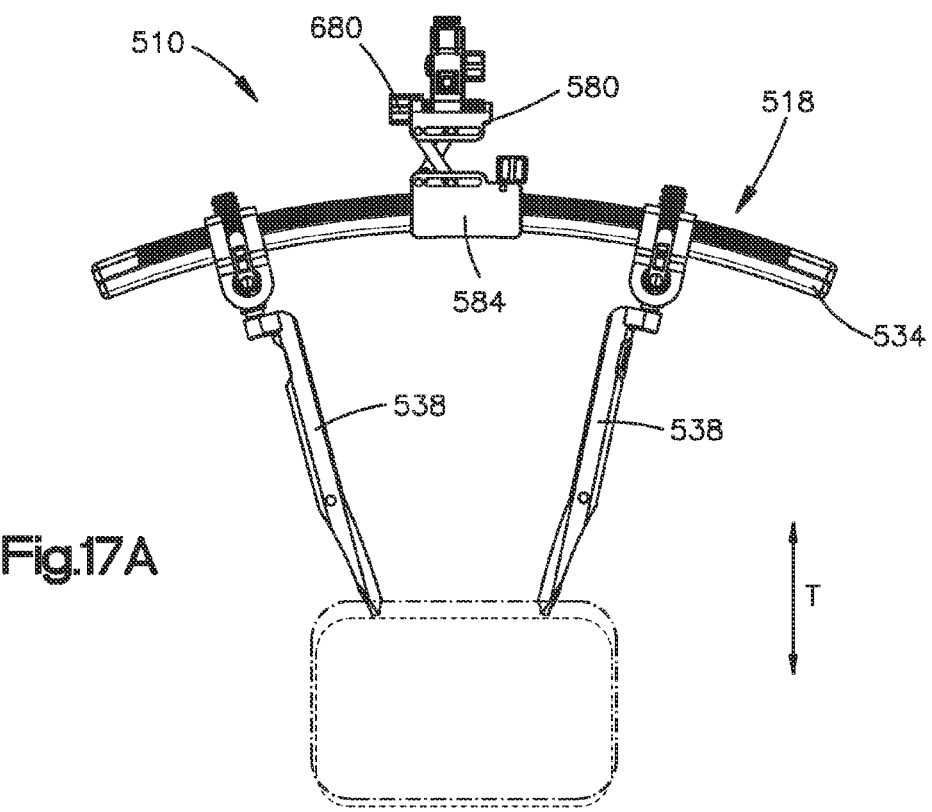
FIG. 17A is a side elevation view of the adjustment system shown in FIG. 9A coupled to vertebral bodies, one of which is misaligned in the transverse direction with respect to the other vertebral bodies.
Figure 17B:
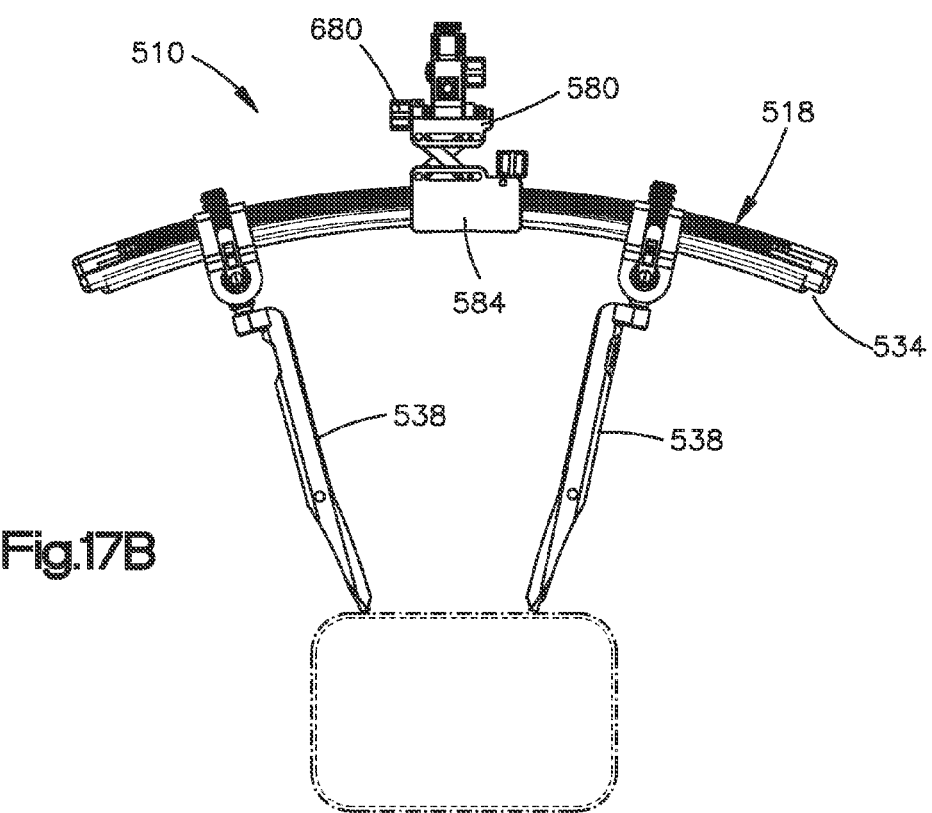
FIG. 17B is a side elevation view of the adjustment system shown in FIG. 17A after the misaligned vertebral body has been moved along the transverse direction.

As shown in FIGS. 17A-17B, the adjustment mechanism may also be activated to move the vertebral bodies along the third or transverse direction. For example, the third adjustment knob 680 may be rotated to thereby cause the second housing 584 to move relative to the first housing 580 along the third or transverse direction. Therefore as shown in FIG. 17B, the vertebral bodies may be moved anteriorly or posteriorly to thereby realign the vertebral bodies as desired. Once aligned, a fixation rod may then be coupled to the bone anchors 30 to thereby stabilize the spine, and the system 510 may be removed.

Figure 18A:
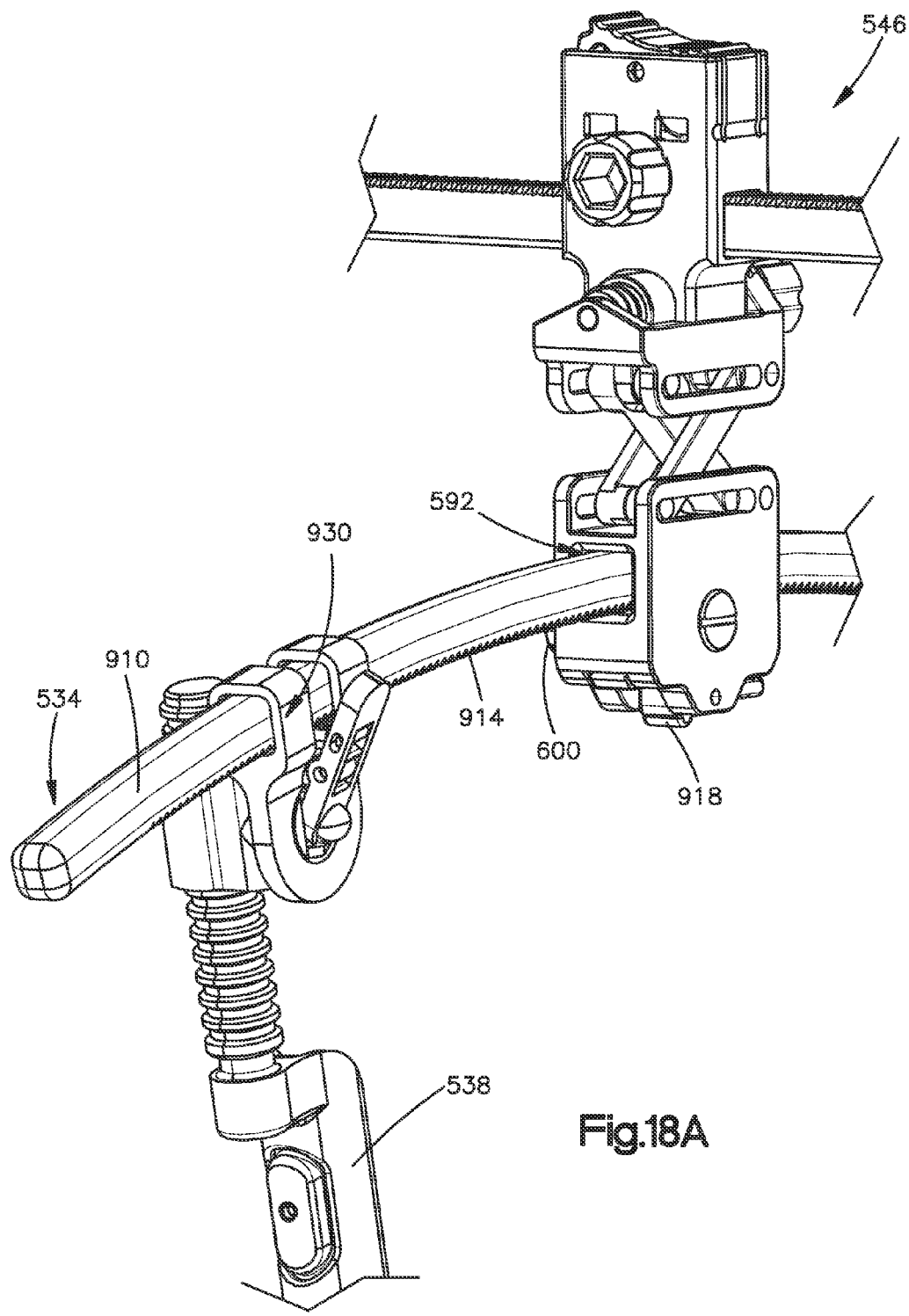
FIG. 18A is a partial perspective view of the adjustment system show in FIG. 10, the adjustment system including a cross-bar and other features in accordance with another embodiment.

As shown in FIGS. 18A and 18B, the cross-bar 534 may include a substantially cylindrical shaped rail 910 and may include engagement members 914 that extend from a bottom surface of the rail 910. In such an embodiment the adjustment mechanism 546 may include a second adjustment knob 604 that extends longitudinally through the second housing 584 and into the second channel 592 so as to engage the engagement members 914 of the cross-bar 534. Moreover, in such an embodiment, the adjustment mechanism 534 may include a release mechanism 918 that when pressed allows the cross-bar 534 to freely translate through the second channel 592.

As shown in FIGS. 18A and 18B, the legs 538 may include locking mechanisms 930 that fixedly couple the legs 538 to the cross-bar 534. As shown, the locking mechanism 930 is constructed similar to the locking mechanism 830 shown in FIG. 14 except that the locking mechanism 930 includes a press button 864 that has teeth 986 that are configured to extend in the transverse direction so as to be able to engage the engagement members 914 of the cross-bar 534.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description. For example, the adjustment knobs may be configured as wing nuts. Furthermore, any features of one described embodiment can be applicable to the other embodiments described herein. For example, each adjustment mechanism or arm described, may be capable of free translation or incremental translation of the cross-bar or elongate members, respectively. Therefore, the adjustment mechanism shown in FIG. 10 may include the release mechanism shown in FIG. 18A to allow the cross-bar to freely translate through the second channel.

What is claimed:

1. A vertebral adjustment system comprising:
a frame having opposed first and second sides that are elongate along respective first and second axes that extend in a longitudinal direction; and
an alignment device configured to be coupled to the frame, the alignment device, comprising:
a first leg including a first end that is configured to be coupled to a respective bone anchor, and a second end spaced from the first end;
a second leg including a first end that is configured to be coupled to a respective bone anchor, and a second end spaced from the first end;
a first adjustment arm including a first elongate member that is elongate along a first axis of elongation, the first elongate member is pivotably coupled to the first side of the frame such that the first adjustment arm is pivotable about the first axis defined by the first side, the first elongate member being further coupled to the first leg such that the first elongate member is further pivotable relative to the second end of the first leg about a respective axis that is oriented along the longitudinal direction, wherein a first length is defined between the second end of the first leg and the first side of the frame, and the first length is adjustable at least by translating the first elongate member along the first axis of elongation; and a second adjustment arm including a second elongate member that is elongate along a second axis of elongation, the second elongate member is pivotably coupled to the second side of the frame such that the second adjustment arm is pivotable about the second axis defined by the second side, the second elongate member being further coupled to the second leg such that the second elongate member is further pivotable relative to the second end of the second leg about a respective axis that is oriented along the longitudinal direction, wherein a second length is defined between the second end of the second leg and the second side of the frame, and the second length is adjustable at least by translating the second elongate member along the second axis of elongation.

2. The system according to claim 1, wherein the first and second adjustment arms are pivotable relative to the second ends of the first and second legs at a pivot location that is spaced from the second ends of the first and second legs.

3. The system according to claim 1, wherein the alignment device further comprises a cross-bar that is coupled to the first and second legs, and the first and second elongate members are pivotably coupled to the cross-bar thereby coupling the first and second elongate members to the first and second legs.

4. The system according to claim 3, wherein the first leg includes a first cross-bar coupler proximate to the second end of the first leg, and the second leg includes a second cross-bar coupler proximate to the second end of the second leg, the first and second couplers couple the first and second legs to the cross-bar.

5. The system according to claim 3, wherein the first adjustment arm includes a first medial housing that pivotably couples the first elongate member to the first side of the frame, and the second adjustment arm includes a second medial housing that pivotablly couples the second elongate member to the second side of the frame, the first and second medial housings each define a respective internal channel that carries an engagement member, the first and second elongate members are received by the respective internal channels such that the engagement member of the first medial housing engages the first elongate member so as to control the adjustability of the first elongate member, and the engagement member of the second medial housing engages the second elongate member so as to control the adjustability of the second elongate member.

6. The system according to claim 5, wherein the engagement members of the first and second medial housings each define internal threads, and the first and second elongate members carry external threads that engage the internal threads, such that rotation of the first elongate member incrementally adjusts the first length and rotation of the second elongate member incrementally adjusts the second length.

7. The system according to claim 5, wherein (i) the first and second medial housings each includes a moveable body portion that carries the engagement member, (ii) the moveable body portion of the first medial housing has a first position in which the engagement member is engaged with the first elongate member, and a second position in which the engagement member is disengaged from the first elongate member so as to allow the first elongate member to freely translate through the channel, and (iii) the moveable body portion of the second medial housing has a first position in which the engagement member is engaged with the second elongate member, and a second position in which the engagement member is disengaged from the second elongate member so as to allow the second elongate member to freely translate through the channel.

8. The system of claim 5, wherein the first and second medial housings each includes a clamp, the clamp of the first medial housing couples the first medial housing to the first side of the frame such that the first medial housing can rotate about the first side, and the clamp of the second medial housing couples the second medial housing to the second side of the frame such that the second medial housing can rotate about the second side of the frame.

9. The system of claim 4, wherein the cross-bar comprises a first elongate rail and a second elongate rail that is parallel to and spaced apart from the first elongate rail to thereby define a gap between the first and second elongate rails.

10. The system of claim 9, wherein the first and second elongate members each defines a respective spherical joint at one end, the spherical joints of the first and second elongate members is disposed within the gap such that the first and second elongate members can pivot with respect to the cross-bar.

11. The system of claim 10, wherein the first and second elongate rails are coupled to each other such that the gap can be reduced to thereby secure the first and second elongate members to the cross-bar.

12. The system of claim 11, wherein the first and second elongate rails each defines an elongate slot that extends therethrough, the slots of the first and second elongate rails are aligned and are configured to receive a locking mechanism to thereby fixedly couple the legs to the first and second elongate rails.

13. The system of claim 12, wherein each cross-bar coupler is disposed within the gap defined between the first and second elongate rails, and defines a respective slot that aligns with the elongate slots of the first and second rails to thereby define a respective through hole.

14. The system of claim 13, wherein the first and second legs each further includes a locking mechanism that extends through the respective through holes and fixedly couples the first and second legs to the cross-bar.

15. The system of claim 14, wherein the first and second rails each defines outer teeth that are engaged by teeth defined by the locking mechanisms when the first and second legs are fixedly coupled to the cross-bar.

16. The system of claim 13, wherein the slots defined by the cross-bar couplers are elongate such that a distance between the cross-bar and the bone anchors is adjustable.

17. The system of claim 3, wherein the frame includes a third side, and the alignment device includes a third adjustment arm that is coupled to the third side of the frame, and pivotally coupled to the cross-bar.

18. The system of claim 17, wherein the first, second, and third sides of the frame are spaced apart from each other so as to define an equilateral triangle.

19. The system of claim 17, wherein the third side is spaced laterally and anteriorly to the first side.

20. The system of claim 3, wherein (i) the bone anchors are configured to be attached to a vertebral body such that the cross-bar, the first leg, the second leg, and the vertebral body define a trapezoidal construct, and (ii) the first and second adjustment arms define first and second linkages of a four-bar linkage mechanism, the trapezoidal construct defines a third linkage of the four-bar linkage mechanism, and the frame defines a fourth linkage of the four-bar linkage mechanism.

21. The system of claim 3, wherein the cross-bar is electrically non-conductive such that each bone anchor is distinguishable during neuromonitoring.

22. The system of claim 1, wherein the first and second axes are elongate along the caudal-cranial direction.

23. The system of claim 22, wherein the first and second axes extend along opposed sides of a spine.

* * * * *